(12) United States Patent
Ohta et al.

(10) Patent No.: US 8,360,638 B2
(45) Date of Patent: *Jan. 29, 2013

(54) RADIOGRAPHIC IMAGING APPARATUS

(75) Inventors: Yasunori Ohta, Kanagawa (JP);
Naoyuki Nishino, Kanagawa (JP);
Naoto Iwakiri, Kanagawa (JP);
Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 212 days.

This patent is subject to a terminal disclaimer.

(21) Appl. No.: 12/954,921

(22) Filed: Nov. 29, 2010

(65) Prior Publication Data

US 2011/0158390 A1 Jun. 30, 2011

(30) Foreign Application Priority Data

Nov. 30, 2009 (JP) ................................. 2009-272756
Nov. 2, 2010 (JP) ................................. 2010-246708

(51) Int. Cl.
*G21K 4/00* (2006.01)
(52) U.S. Cl. .................... 378/190; 250/370.09
(58) Field of Classification Search .................... 378/62, 378/98.8, 154, 189, 190; 250/370.08, 370.09
See application file for complete search history.

(56) References Cited

U.S. PATENT DOCUMENTS

2011/0127440 A1 * 6/2011 Ohta et al. ............... 250/370.08

FOREIGN PATENT DOCUMENTS

| JP | 2000-10220 A | 1/2000 |
| JP | 2003-339687 A | 12/2003 |
| JP | 2004-173908 A | 6/2004 |
| JP | 2009-80103 A | 4/2009 |

* cited by examiner

*Primary Examiner* — Courtney Thomas
(74) *Attorney, Agent, or Firm* — SOLARIS Intellectual Property Group, PLLC

(57) ABSTRACT

There is provided a radiographic imaging apparatus including: a control unit housing a control section and a power source section; a panel unit housing a radiation detection panel; a connection member that rotatably connects one edge portion of each of the control unit and the panel unit so as to adopt two states: a closed state in which one face of the control unit faces one face of the panel unit, and an open state in which the one face of the control unit and the one face of the panel unit are side-by-side facing in substantially the same direction, wherein in the open state the other face of the panel unit is positioned higher than the other face of the control unit; and a support member positioned below the other face of the panel unit and supporting the panel unit when in the open state.

19 Claims, 25 Drawing Sheets

CLOSE STATE

RADIOGRAPHIC IMAGING APPARATUS

CROSS-REFERENCE TO RELATED APPLICATION

This application is based on and claims priority under 35 USC 119 from Japanese Patent Applications No. 2009-272756 filed on Nov. 30, 2009 and No. 2010-246708 filed on Nov. 2, 2010, the disclosures of which are incorporated by reference herein.

BACKGROUND

1. Technical Field

The present invention relates to an radiographic imaging apparatus, and in particular to a radiographic imaging apparatus provided with a radiation detection panel.

2. Related Art

FPD's (Flat Panel Detectors) that have a radiation sensitive layer disposed on a Thin Film Transistor (TFT) active matrix substrate, detect irradiated radiation, such as X-rays, and directly convert this radiation into radiographic image data expressing the distribution of irradiated radiation amounts are being put into practice. Portable radiographic imaging apparatuses (sometimes referred to below as "electronic cassettes") that house a panel type radiation detector, such as one of the above FPDs, a control section including a memory section, and a power source section, also being put into practice for storing in the image memory radiographic image data output from the radiation detector. Due to excellent portability, the electronic cassettes can capture images of investigation subjects still lying on a stretcher or bed, and the imaging location can be readily adjusted by changing the position of the electronic cassette. Hence electronic cassettes can be flexibly adopted for cases of image capture for an investigation subject not able to move.

Related to the above, a technique is described in Japanese Patent Application Laid-Open (JP-A) No. 2003-339687 with an object of realizing image capture from plural directions with an expanded surface area of a flat panel sensor, together with portability and ease of handling. In this technique, a structure capable of opening and closing is described of two plates of flat panel sensor that are joined at edges on one side of each, in an image capture apparatus, such as an electronic cassette, having a flat panel sensor.

A technique is described in JP-A No. 2004-173908 with an object to reduce the physical burden on an operative. In this technique, an electronic cassette (image capture section) is separated from an image control section, the electronic cassette is set in a vertical state in the stage of an auxiliary device, and during image capture, by operating a hydraulic cylinder coupled to the stage, the stage (the detection face of the electronic cassette) is raised to the horizontal.

A technique is described in JP-A No. 2009-80103 with an object to reduce the weight of a cassette system. In this technique, a control unit mounted with electronic components, such as an interface circuit section, a cassette control section, and a communication unit, is configured so as to be separable from a cassette having a radiation detector using a connector and cable, and the control unit is separated from the cassette during image capture.

A technique is described in JP-A No. 2000-10220 with an object of protecting a compact, thin, X-ray detection means during carrying and handling. The X-ray image capture apparatus described has a panel case provided with X-ray detection means, and a control case provided with control means, with these two cases configured so as to be rotatably connected.

A radiographic imaging apparatus, such as an electronic cassette, is configured including a large number of electronic components, particularly in the control section and power source section. Since electronic components with high heat generation amount are employed in part, accompanying a rise in internal temperature of the radiographic imaging apparatus due to heat generation from electronic components, problems sometimes arise such as changes to the electrical characteristics of the radiation detector (such as, for example, increase in noise, increase in dark current flow of the TFTs, and the like), and deterioration in the radiation detector (such as, for example, deformation and damage due to the layered structure of the radiation detector with different thermal expansion coefficients for each member, deterioration and delamination of a bonding member due to repeated changes in temperature, crystallization of amorphous selenium accompanying temperature rises for direct conversion type radiation detectors, and the like). In addition, there are occasions when an unpleasant sensation is imparted to an investigation subject due to excessive rise in surface temperature of the radiographic imaging apparatus. In particular, the above problems are even more significant during video image capture, such as in radiographic guidance, where the amount of heat generated is large in comparison to still image capture due to performing continuous image capture (over a long duration). There is a possibility that counter measures need to be taken which themselves lead to an adverse impact on the ease of use, such as, for example, limiting the duration of continuous operation or the like.

To address this issue, JP-A No. 2009-80103 has an object of suppressing changes in structure (crystallization) of amorphous selenium that configures a portion of the radiation detector. There is a proposal to dispose means to cool the radiation detector within the cassette, however, this leads to problems of the configuration of the radiographic imaging apparatus becoming complicated, and a large increase in the power consumption of the radiographic imaging apparatus due to configuring the cooling means. Heat dissipation or cooling of the radiation detector are not really considered in the techniques of JP-A Nos. 2003-339687, 2004-173908 and 2000-10220.

In order to address these problems, a technique might be considered that employs the techniques of JP-A No. 2003-339687 and JP-A No. 2000-10220, namely: configuring a control unit housing a control section and a power source section and a panel unit housing a radiation detection panel as separate bodies, and rotatably connecting one edge portion of each of the control unit and the panel unit together with a connection member, so as to adopt two states, a closed state in which one face of the control unit faces one face of the panel unit, and an open state in which the one face of the control unit and the one face of the panel unit are side-by-side and face in substantially the same direction.

However, in such a case, in the open state the other face of the panel unit (the face that faces downwards) is sometimes positioned above the other face of the control unit (the face that faces down). In such a case, if image capture is performed in a state in which the investigation subject is placed on top of the radiographic imaging apparatus, then new problems sometimes arise, such as load from the investigation subject resulting in distortion of the panel unit, leading to the images obtained by image capture being distorted, and even leading to breakage of the radiation detection panel.

Namely, the radiation detection panel can be formed by a glass substrate, similarly to a liquid crystal display, and can be made comparatively thin. However, circuit elements employed in the control unit, such as an inductance circuit, coil, or the like, and a battery and the like employed in the power source section, often have a height that is higher than that of the radiation detection panel. In such cases, as a result of making the panel unit thinner than the control unit, there is a high possibility that the bottom face of the panel unit is positioned above the bottom face of the control unit.

In order to realize an electronic cassette of the shape and size (thickness about 16 mm) that can be set in an imaging stage or the like similar to that of existing film cassettes, inevitably the thicknesses of the panel unit and the control unit are different, with the panel unit required to be as thin as possible. Furthermore, in order to suppress an unpleasant feeling of an investigation subject, heat generating portions, such as the control section and the power source section, are housed in the control unit wherever possible, and the panel unit inevitably becomes thinner by a corresponding amount. As the size of any gap between the outer surface of the panel unit and the radiation detection panel surface increases, the distance between the imaging subject and the radiation detection panel increases, and since this leads to blurring of the images this gap should be made as small as possible. As a result the panel unit inevitably become thinner. In such cases too, as a result of the panel unit being relatively thinner than the control unit, there is a high possibility that the bottom face of the panel unit is positioned higher than the bottom face of the control unit.

SUMMARY

The present invention addresses the above problems, and an object thereof is to provide a radiographic imaging apparatus that can prevent deterioration in quality of images obtained by image capture and prevent breakage of the radiation detection panel, while suppressing temperature rise of the radiation detection panel.

In order to achieve the above object, a first aspect of the present invention provides a radiographic imaging apparatus including:

a control unit housing a control section and a power source section;

a panel unit housing a radiation detection panel;

a connection member that rotatably connects one edge portion of each of the control unit and the panel unit so as to adopt two states: a closed state in which one face of the control unit faces one face of the panel unit, and an open state in which the one face of the control unit and the one face of the panel unit are side-by-side facing in substantially the same direction, wherein in the open state the other face of the panel unit is positioned higher than the other face of the control unit; and a support member positioned below the other face of the panel unit and supporting the panel unit when in the open state.

The radiographic imaging apparatus of the first aspect has the control section and the power source section housed by the control unit, and has the radiation detection panel housed by the panel unit.

In the present invention, one edge portion of the control unit and the panel unit respectively are rotatably connected by the connection member so as to adopt two states, the closed state in which one face of the control unit faces one face of the panel unit, and the open state in which the one face of the control unit and the one face of the panel unit are side-by-side and face in substantially the same direction, and in the open state, the other face of the panel unit is positioned higher than the other face of the control unit.

In the present invention, when in the open state, the panel unit is supported by the support member positioned below the other face of the panel unit.

Namely, in the present invention, the control section and the power source section that are large heat generation sources are housed in the control unit, and the radiation detection panel is housed in the panel unit. One edge of the control unit and the panel unit respectively are rotatably connected together using the connection member so as to adopt two states, the closed state in which one face of the control unit faces one face of the panel unit, and the open state in which the one face of the control unit and the one face of the panel unit are side-by-side and face in substantially the same direction. Consequently, as a result of being able to weaken thermal coupling of the control section and the power source section to the radiation detection panel, rise in temperature of the radiation detection panel can be suppressed.

In the present invention, in the above open state, the other face of the panel unit is positioned higher than the other face of the control unit. However, in the present invention, as a result of the panel unit being supported by the support member positioned below the other face of the panel unit, distortion of the panel unit can be prevented, and deterioration in quality of images obtained by image capture and breakage of the radiation detection panel caused by such distortion can be prevented.

According to the radiographic imaging apparatus of the first aspect, the control section and the power source section are housed by the control unit, and the radiation detection panel is housed by the panel unit, one edge portion of the control unit and the panel unit respectively are rotatably connected by the connection member so as to adopt two states, the closed state in which the one face of the control unit and the one face of the panel unit are in a facing state, and the open state in which the one face of the control unit and the one face of the panel unit are side-by-side and facing in substantially the same direction, and in the open state the support member that supports the panel unit is positioned below the other face of the panel unit. Consequently, deterioration in quality of images obtained by image capture and breakage of the radiation detection panel can be prevented, while suppressing temperature rise of the radiation detection panel.

A second aspect of the present invention provides the radiographic imaging apparatus of the first aspect, wherein the support member is configured so as to be attachable to and detachable from the panel unit.

Due thereto, ease of use can be enhanced.

A third aspect of the present invention provides the radiographic imaging apparatus of the first aspect, wherein in the open state, the one face of the control unit that faces the panel unit in the closed state and the one face of the panel unit are at substantially the same height.

Due thereto, when performing image capture in a state in which the investigation subject is placed on the radiographic imaging apparatus, problems arising due to a difference in level between the other face of the control unit and the other face of the panel unit can be prevented.

A fourth aspect of the present invention provides the radiographic imaging apparatus of the first aspect, wherein the support member is a member comprising a grid that removes scattered rays of radiation due to an imaging subject during image capture.

Due thereto, scattered rays of radiation due to the investigation subject during image capture can be removed.

A fifth aspect of the present invention provides the radiographic imaging apparatus of the first aspect, wherein the support member is a member comprising lead that prevents back scattering during image capture.

Due thereto, back scattering during image capture can be prevented.

A sixth aspect of the present invention provides the radiographic imaging apparatus of the first aspect, wherein the support member is a member comprising a battery.

Due thereto, the region required for the above power source section can be reduced.

A seventh aspect of the present invention provides the radiographic imaging apparatus of the first aspect, wherein the support member is a handle provided at a peripheral edge portion of the panel unit.

Due thereto, the above support member can have the dual use as a handle.

An eighth aspect of the present invention provides the radiographic imaging apparatus of the first aspect, wherein the radiation detection panel is capable of detecting radiation from both a front face and a back face.

Due thereto, radiographic image capture can be performed in one or other state from the closed state and the open state.

A ninth aspect of the present invention provides the radiographic imaging apparatus of the eighth aspect, further including a detection component for detecting whether the control unit and the panel unit are in out of the closed state or the open state, wherein, the control section controls such that still image capture is performed in cases in which the closed state has been detected by the detection component, and controls such that video image capture is performed in cases in which the open state has been detected.

Due thereto, as a result of being able to perform image capture during still image capture with the panel unit and the control unit in a superimposed state, breakage of the radiation detection panel can be prevented, and as a result of being able to expand the surface area during video image capture, the heat dissipation effect can be enhanced for video image capture having higher heat generation than the still image capture.

A tenth aspect of the present invention provides the radiographic imaging apparatus of the first aspect, wherein the control unit comprises, on the one face, an operation section, a display section, or a combination thereof.

Due thereto, in the closed state, the operation section and/or the display section provided to the control unit can be protected, and when the operation section is present, unintentional operation of the operation section can be prevented when in the closed state.

An eleventh aspect of the present invention provides the radiographic imaging apparatus of the first aspect, wherein the support member is displaceably configured so as to be inset to the control unit when in the closed state, and to be positioned below the other face of the panel unit when in the open state.

Due thereto, the portability of the radiographic imaging apparatus can be enhanced.

A twelfth aspect of the present invention provides the radiographic imaging apparatus of the first aspect, wherein the radiation detection panel comprises a substrate formed with switch elements and layered with a charge generation layer that generates charge by irradiation with radiation, the switch elements accumulate charge generated by the charge generation layer and read out the charge, with the radiation detection panel installed in the panel unit such that the charge generation layer is on the one face side of the panel unit.

A thirteenth aspect of the present invention provides the radiographic imaging apparatus of the first aspect, wherein an amplification circuit for amplifying an electrical signal output from a radiation detection panel, an A/D converter for converting the electrical signal amplified by the amplification circuit to digital image data, or a combination thereof, is provided inside the connection member.

Due thereto, the cooling effect can be enhanced for the amplification circuit and/or the A/D converter, and also a need to secure a region for providing the amplification circuit and/or the A/D converter in the control unit or the panel unit is removed.

A fourteenth aspect of the present invention provides the radiographic imaging apparatus of the first aspect, wherein the control unit further comprises a communication section that performs communication with an external device.

Due thereto, the ease of use can be enhanced.

A fifteenth aspect of the present invention provides the radiographic imaging apparatus of the fourteenth aspect, wherein the communication section is a wireless communication section that performs wireless communication with the external device.

Due thereto, as a result of being able to separate the antenna employed in wireless communication from the investigation subject, generation of transmission interference can be suppressed.

A sixteenth aspect of the present invention provides the radiographic imaging apparatus of the first aspect, wherein a surface of the control unit is formed in an undulating shape.

Due thereto, as a result of being able to expand the surface area of the control unit, the heat dissipation effect can be enhanced.

A seventeenth aspect of the present invention provides the radiographic imaging apparatus of the first aspect, wherein a thickness of the panel unit is thinner than a thickness of the control unit.

Due thereto, the effect of preventing damage to the radiation detection panel can be exhibited at an even higher level.

An eighteenth aspect of the present invention provides the radiographic imaging apparatus of the first aspect, wherein:

the radiation detection panel is configured such that radiation is converted into light in a scintillator for converting radiation into light and the radiation detection panel outputs an electrical signal expressing a radiographic image representation of this light; and the scintillator is configured including columnar crystals of a fluorescent material.

A twentieth aspect of the present invention provides the radiographic imaging apparatus of the eighteenth aspect, wherein the fluorescent material is CsI.

According to the radiographic imaging apparatus of the present invention, the control section and the power source section are housed by the control unit, and the radiation detection panel is housed by the panel unit, one edge portion of the control unit and the panel unit respectively are rotatably connected by the connection member so as to adopt two states, the closed state in which the one face of the control unit faces the one face of the panel unit, and the open state in which the one face of the control unit and the one face of the panel unit are side-by-side and facing in substantially the same direction, and in the open state the support member that supports the panel unit is positioned below the other face of the panel unit. Consequently, deterioration in quality of images obtained by image capture and breakage of the radiation detection panel can be prevented, while suppressing temperature rise of the radiation detection panel.

BRIEF DESCRIPTION OF THE DRAWINGS

Exemplary embodiments of the present invention will be described in detail based on the following figures, wherein.

DETAILED DESCRIPTION

Detailed explanation follows regarding exemplary embodiments for implementing the present invention.

Figure 1:
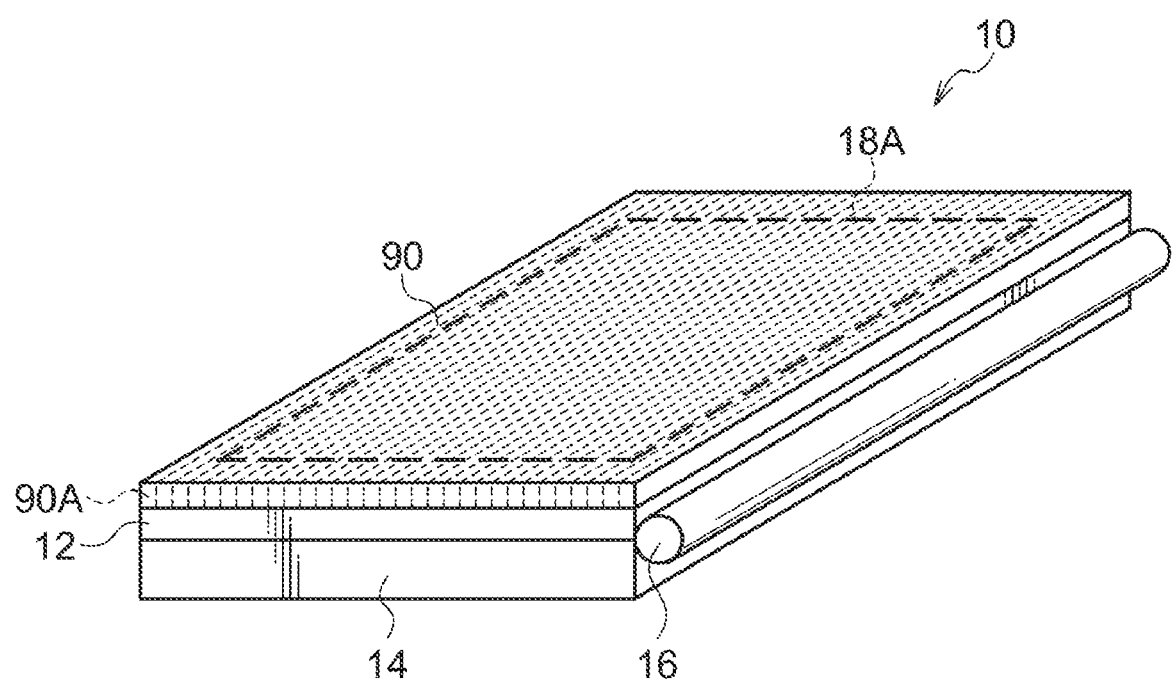
FIG. 1 is a perspective view showing a configuration of an electronic cassette according to a present exemplary embodiment (in the closed state)
Figure 2:
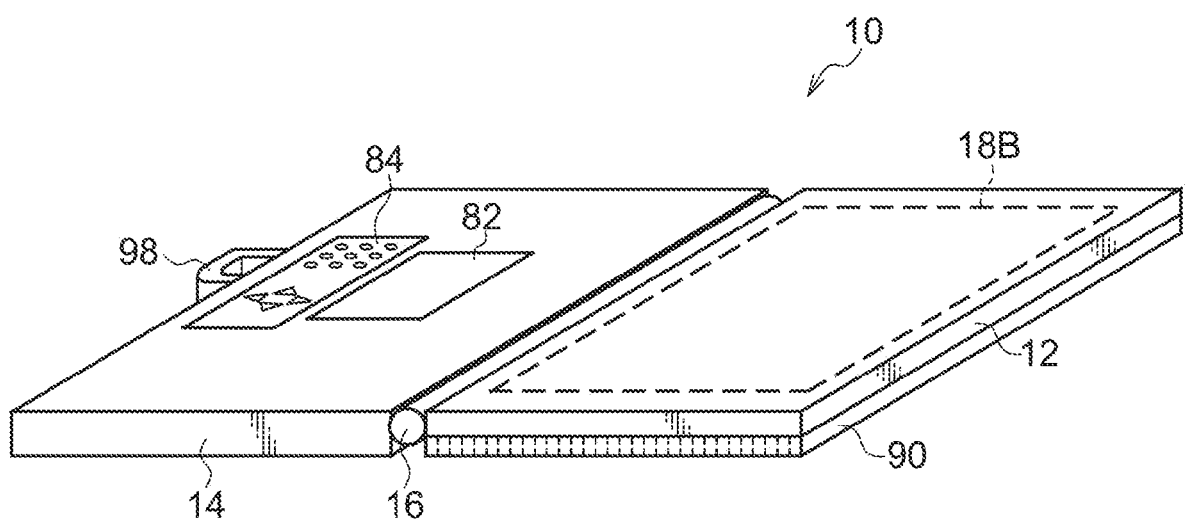
FIG. 2 is a perspective view showing a configuration of an electronic cassette according to the present exemplary embodiment (in the open state)

FIG. 1 and FIG. 2 show perspective views of a configuration of an electronic cassette 10 according to the present exemplary embodiment.

As shown in FIG. 1, the electronic cassette 10 is provided with: a flat plate shaped panel unit 12, in which a radiation detection panel 20 (see FIG. 3), described below, is housed for capturing a radiographic image from irradiated radiation and; and a flat plate shaped control unit 14 in which a control section 50 (see FIG. 3), described below, is housed for controlling image capture operation of the radiation detection panel 20. Edge portions of the panel unit 12 and the control unit 14 are connected together by a hinge 16.

The panel unit 12 and the control unit 14 are openable and closeable by rotation of one with respect to the other about the hinge 16, so as to adopt an open state (the state shown in FIG. 2A and FIG. 2B) in which the panel unit 12 and the control unit 14 are side-by-side, and a closed state (the state shown in FIG. 1) in which the panel unit 12 and the control unit 14 are folded together and superimposed on top of each other.

As shown in FIG. 1 and FIG. 2, when the electronic cassette 10 according to the present exemplary embodiment is in the closed state, one face of the panel unit 12 and one face of the control unit 14 are in a facing state, and when in the open state, the face mentioned above of the panel unit 12 and the face mentioned above of the 14 adopt a state in which they are both in the same flat plane, next to each other side-by-side and facing in substantially the same direction.

In the electronic cassette 10 according to the present exemplary embodiment, as shown in FIG. 2, configuration is made such that any difference in level between the panel unit 12 and the control unit 14 disappears when in the open state.

The control unit 14 is provided, on the face that faces the panel unit 12 in the closed state, with a display section 82 equipped with a display device capable of displaying an image or the like, and an operation section 84 equipped with various buttons, such as a cross-key, a ten-key and the like. A handle 98 is provided to the control unit 14 for gripping when moving the electronic cassette 10. Note that while in the electronic cassette 10 according to the present exemplary embodiment the handle 98 is provided at a central portion on the side wall of the control unit 14 that is on the opposite side to the side wall on which the hinge 16 is provided, there is no limitation thereto. For example, obviously the handle 98 may be provided in another position other than this side wall, such as at a central portion of any other of the side walls on which the hinge 16 is not provided, or in a position shifted from the central portion of these side walls by a distance that takes account of the eccentricity in the position of the center of gravity of the electronic cassette 10.

In the electronic cassette 10 according to the present exemplary embodiment, on the face of the panel unit 12 that is opposite to the face opposing the control unit 14 when in the closed state, a flat plate shaped support member 90 is provided, housing a grid 90A for removing scattered rays of radiation due to the investigation subject during image capture.

The support member 90 according to the present exemplary embodiment has substantially the same shape and dimensions in plan view as that of the panel unit 12, and the thickness is a thickness that is substantially the height from the bottom face of the panel unit 12 to the bottom face of the control unit 14, namely the vertical direction distance to the placement surface of the electronic cassette 10, when in the open state. The support member 90 has the role of removing scattered rays of radiation due to the investigation subject during image capture, as well as the role of supporting the panel unit 12 when in the open state.

In the electronic cassette 10 according to the present exemplary embodiment, while the support member 90 is bonded to the panel unit 12 with a bonding agent, there is no limitation thereto, and obviously configuration may be made with attraction by magnetic force, fitting through a fitting member, or the like. In such cases, since the support member can be made attachable and detachable, the support member 90 can be removed when not image capturing, and portability can be enhanced.

Figure 3:
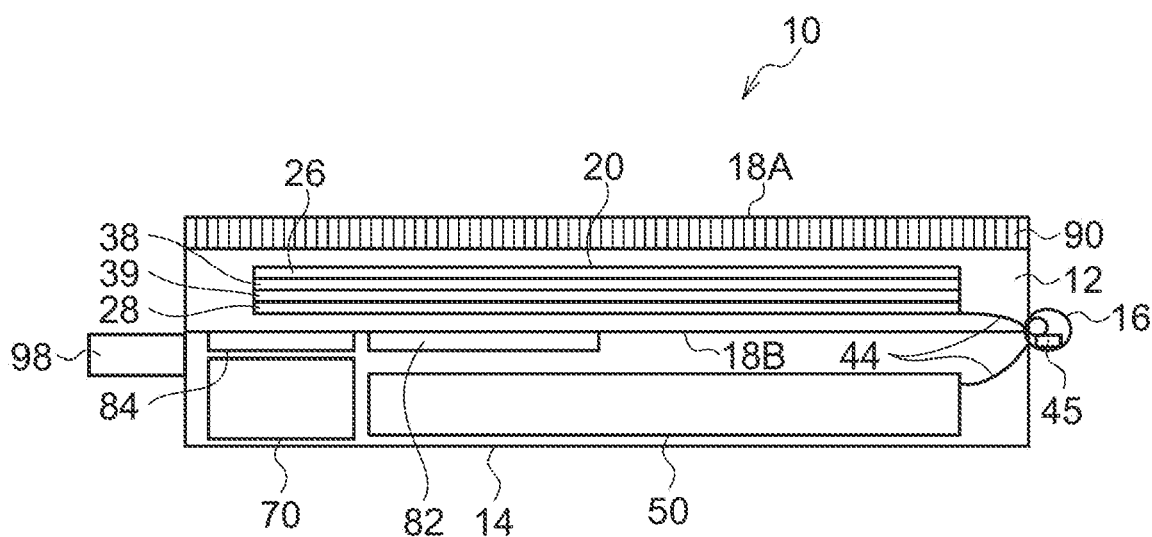
FIG. 3 is a lateral cross-section showing a configuration of an electronic cassette according to the present exemplary embodiment (in the closed state)

FIG. 3 shows a lateral cross-section of the electronic cassette 10 according to the present exemplary embodiment in the closed state.

As shown in FIG. 3, the panel unit 12 according to the present exemplary embodiment houses the radiation detection panel 20 that captures a radiographic image expressing irradiated radiation, and outputs an electrical signal representing the captured radiographic image. The control unit 14 according to the present exemplary embodiment houses the control section 50 for controlling image capture operation of the radiation detection panel 20 and a power source section 70 for supplying driving power to the control section 50 and the like.

The radiation detection panel 20 and the control section 50 are connected together electrically through connection wiring 44 provided through the hinge 16.

An open-close sensor 45 is provided to the hinge 16, for detecting open or closed states of the panel unit 12 and the control unit 14. The open-close sensor 45 may be configured, for example: to detect the above open and closed states by detecting changes in magnetic field due to opening and closing the panel unit 12 and the control unit 14 with a combination of a magnet and a Hall sensor; to detect the open or closed states using an angular sensor that detects the open-close angle between the panel unit 12 and the control unit 14; or to detect the open or closed states using plural mechanical switches disposed such that the combination of ON states and OFF states changes due to the open and closed states of the panel unit 12 and the control unit 14.

Figure 4:
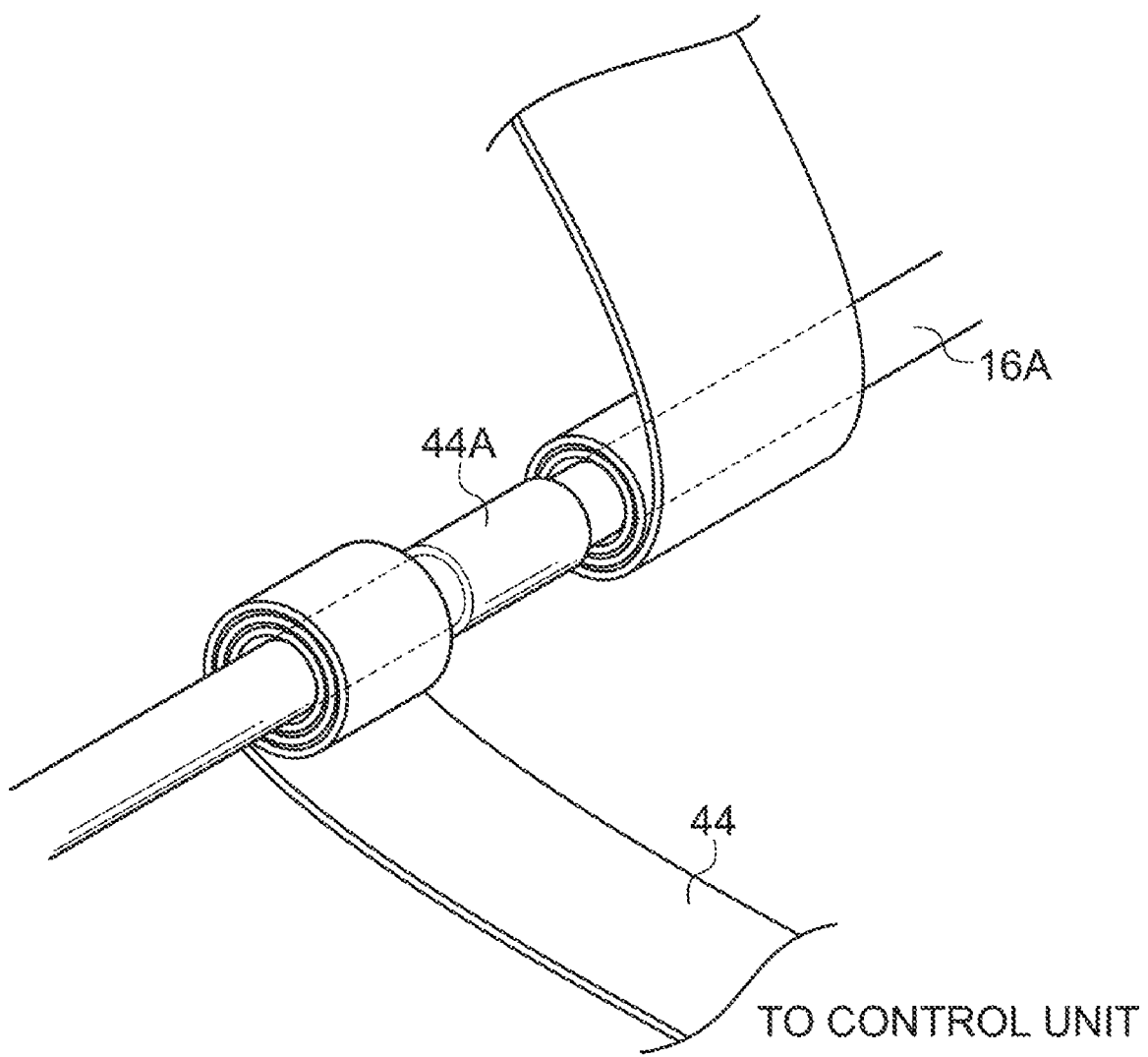
FIG. 4 is a perspective view showing a configuration of connection wiring inside a hinge in an electronic cassette according to the present exemplary embodiment.

Due thereto, since the panel unit 12 and the control unit 14 are openable and closeable using the hinge 16, the hinge 16 portion of the connection wiring 44 is susceptible to breaks and damage occurring due to not withstanding bending, or due to application of bending stress thereto. Therefore, in the electronic cassette 10 according to the present exemplary embodiment, the connection wiring 44 is formed by a flexible printed circuit board of crank shape in plan view. As an example thereof, shown in FIG. 4, after a cylindrical portion 44A has been formed by winding a central portion of the connection wiring 44 plural times on the rotation shaft 16A of the hinge 16 that supports the panel unit 12 and the control unit 14 in an openable and closeable manner, tape is wound on the external periphery to fix and retain the cylindrical portion 44A. Then the connection wiring 44 at the two sides of the cylindrical portion 44A is wound on the rotation shaft 16A with plural turns in a loose spiral shape and led out towards the panel unit 12 and the control unit 14, respectively.

Accordingly, when the panel unit 12 and the control unit 14 are opened or closed, the connection wiring 44 along the rotation shaft 16A rotates, since the connection wiring 44 at the two sides of the cylindrical portion 44A have only been wound loosely on the rotation shaft 16A, the two sides follow the opening or closing of the panel unit 12 and the control unit 14 in an extremely flexible manner, such that there is no damage to the connection wiring 44.

Explanation now follows of a configuration of the radiation detection panel 20 according to the present exemplary embodiment, with reference to FIGS. 5-10.

Figure 5:
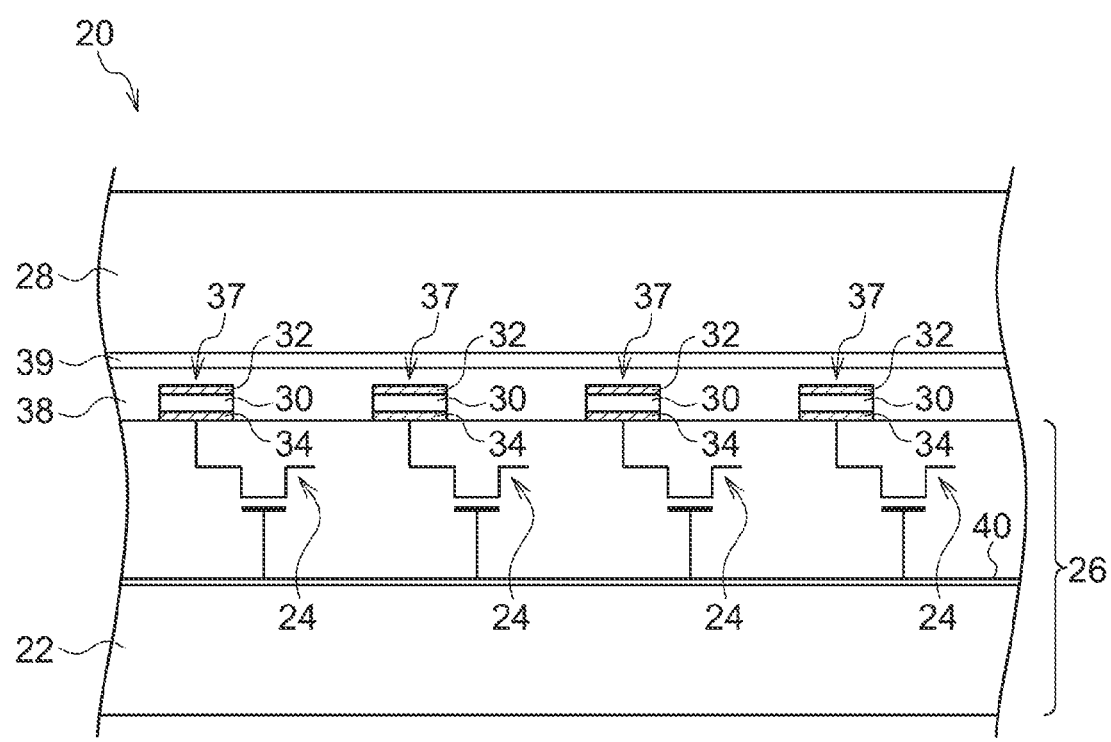
FIG. 5 is a cross-section showing a configuration of a radiation detection panel according to the present exemplary embodiment.

As shown in FIG. 5, the radiation detection panel 20 according to the present exemplary embodiment is provided with a TFT substrate 26 with switch elements 24, such as, for example, Thin Film Transistors (TFT) or the like formed to an insulating substrate 22.

A scintillator layer 28 is formed over the TFT substrate 26, serving as an example of a radiation conversion layer and converting irradiated radiation into light.

Materials that can be employed as the scintillator layer 28 include, for example, CsI:Tl and GOS ($Gd_2O_2S$:Tb). Note that the scintillator layer 28 is not limited to these materials. For the insulating substrate 22, for example, a glass substrate, various types of ceramic substrate, or a resin substrate can be employed. The insulating substrate 22 is also not limited to these materials.

Preferably the wavelength region of emission light for the scintillator layer 28 is in the visible light region (wavelengths from 360 nm to 830 nm), and more preferably includes a green wavelength region to enable monochrome image capture with the radiation detection panel 20.

Specifically, fluorescent bodies employed in the scintillator layer 28 preferably include cesium iodide (CsI) for cases in which X-rays are employed as radiation, and particularly preferably use thallium doped cesium iodide (CsI (Tl)) having an emission spectrum during X-ray irradiation of wavelength 420 nm to 600 nm. The emission peak wavelength of CsI (Tl) in the visible light region is at 565 nm.

Vapor deposition onto a vapor deposition substrate may be employed for cases in which the scintillator layer 28 is to be formed, for example, by columnar crystals of CsI (Tl) or the like. Often an Al plate is employed for the vapor deposition substrate in cases in which the scintillator layer 28 is formed thus by vapor deposition, due to its X-ray transmissivity and cost perspective, however there is no limitation thereto. For cases in which GOS is employed as the scintillator layer 28, the scintillator layer 28 may be formed by coating GOS on the front face of the TFT substrate 26 without using a vapor deposition substrate.

Photoconducting layers 30 are disposed between the scintillator layer 28 and the TFT substrate 26. The photoconducting layers 30 generate charge on being irradiated with light that has been converted by the scintillator layer 28. Bias electrodes 32 are formed on the surface of the photoconducting layers 30, on the scintillator layer 28 side thereof. The bias electrodes 32 apply a bias voltage to the photoconducting layers 30.

The photoconducting layers 30 absorb light that has been generated from the scintillator layer 28, and generates charge according to the light that has been absorbed. The photoconducting layers 30 may be formed from a material that generates charge on irradiation with light, and can, for example, be formed from amorphous silicon, an organic photoelectric conversion material, or the like. Photoconducting layers 30 containing amorphous silicon have a wide absorption spectrum and can absorb light that has been generated in the scintillator layer 28. Photoconducting layers 30 containing an organic photoelectric conversion material have an absorption spectrum with a sharp peak in the visible light region, and there is substantially no absorption by the photoconducting layers 30 of electromagnetic waves other than the light generated by the scintillator layer 28, thereby enabling effective suppression of noise generation by absorption of radiation, such as X-rays, in the photoconducting layers 30.

In order for an organic photoelectric conversion material configuring the photoconducting layers 30 to exhibit the most effective absorption of light generated in the scintillator layer 28, the absorption peak wavelength of the organic photoelectric conversion material is preferably as close as possible to the light generation peak wavelength of the scintillator layer 28. While ideally the absorption peak wavelength of the organic photoelectric conversion material matches the light generation peak of the scintillator layer 28, it is possible to achieve sufficient absorption of light emitted from the scintillator layer 28 as long as the difference between the two wavelengths is small. Specifically, the difference between the organic photoelectric conversion material absorption peak wavelength and the light generation peak wavelength of the scintillator layer 28 in response to radiation is preferably 10 nm or less, and more preferably 5 nm or less.

Examples of organic photoelectric conversion materials capable of meeting such criteria include, for example, quinacridone organic compounds and phthalocyanine organic compounds. For example, due to the peak absorption wavelength of quinacridone in the visible light region being 560 nm, it is possible to make the difference between the above two pack wavelengths 5 nm or less by employing quinacridone as the organic photoelectric conversion material and employing CsI (Tl) at the material for the scintillator layer 28. This enables substantially the maximum amount of charge to be generated in the photoconducting layers 30.

Charge collection electrodes 34 are formed on the TFT substrate 26 to collect charge that has been generated in the photoconducting layers 30. In the TFT substrate 26, the charge collected in each of the charge collection electrodes 34 is read by the switch elements 24.

Explanation now follows regarding specifics of the photoconducting layers 30 applicable to the radiation detection panel 20 according to the present exemplary embodiment.

The electromagnetic wave absorption/photoelectric conversion locations in the radiation detection panel 20 according to the present invention can each be configured by a pair of electrodes, a collection electrode 34 and a bias electrode 32, and by organic layers including one of the photoconducting layers 30 disposed between the collection electrode 34 and the bias electrode 32. More specifically, the organic layers can be configured with, for example, a location for electromagnetic wave absorption, a location for photoelectric conversion, an electron transport location, a hole transport location, an electron blocking location, a hole blocking location, a crystallization prevention location, an electrode, an interlayer adhesion improvement location and the like, either superimposed on each other in layers or mixed.

The above organic layers preferably include a p-type organic compound or an n-type organic compound.

Organic p-type semiconductors (compounds) are mainly organic compounds that are donor organic semiconductors (compounds), typified by organic compounds with hole transport properties, and have the property that they readily donate electrons. More specifically they are organic compounds that have the smaller ionization potential when two organic materials are placed in contact with each other. Accordingly, any organic compound may be employed as a donor organic compound as long as it is an organic compound with electron donating properties.

Organic n-type semiconductors (compounds) are mainly organic compounds that are acceptor organic semiconductors (compounds), typified by organic compounds with electron transport properties, and have the property of readily accepting electrons. More specifically, they are organic compounds that have the larger ionization potential when two organic materials are placed in contact with each other. Accordingly, any organic compound may be employed as an acceptor organic compound as long as it is an organic compound with electron accepting properties.

Since there is explanation of details regarding applicable materials for organic p-type semiconductors and organic n-type semiconductors to configure the photoconducting layers 30 given in JP-A No. 2009-32854, further explanation is omitted. Note that the photoconducting layers 30 may be formed so as to further include fullerenes and/or carbon nanotubes.

Sensor portions 37 configuring each of the pixel portions should at least include the collection electrode 34, the photoconducting layer 30, and the bias electrode 32. However, they are preferably also provided with one or other of an electron blocking layer or a hole blocking layer in order to suppress dark current from increasing, and are more preferably provided with both.

The electron blocking layer can be provided between the collection electrode 34 and the photoconducting layer 30, enabling suppression of an increase in dark current from electrons being injected into the photoconducting layer 30 from the collection electrode 34 when a bias voltage is applied between the collection electrode 34 and the bias electrode 32.

An electron donor organic compound can be employed as the electron blocking layer.

The material actually employed as the electron blocking layer may be selected according to the material of the adjacent electrode and material of the adjacent photoconducting layer 30. A material is preferably employed having an electron affinity (Ea) that is at least 1.3 eV more than the work function (Wf) of the material of the adjacent electrode, and an ionization potential (Ip) that is about the same as, or smaller than, the Ip of the material of the photoconducting layer 30. Since there is explanation of details regarding applicable materials as such an electron donor organic material given in JP-A No. 2009-32854 further explanation thereof is omitted.

The thickness of the electron blocking layer is preferably 10 nm to 200 nm in order to reliably exhibit a dark current suppressing effect and also to prevent a drop in photoelectric conversion efficiency of the sensor portions 37. A thickness thereof of 30 nm to 150 nm is more preferable, and a thickness of 50 nm to 100 nm is even more preferable.

The hole blocking layer can be provided between the photoconducting layer 30 and the bias electrode 32, enabling suppression of an increase in dark current from holes being injected into photoconducting layer 30 from the bias electrode 32 when a bias voltage is applied between the collection electrode 34 and the bias electrode 32.

An electron acceptor organic compound can be employed as the hole blocking layer.

The thickness of the hole blocking layer is preferably 10 nm to 200 nm in order to reliably exhibit a dark current suppressing effect and also to prevent a drop in photoelectric conversion efficiency of the sensor portions 37. A thickness thereof of 30 nm to 150 nm is more preferable, and a thickness of 50 nm to 100 nm is even more preferable.

The material actually employed as the hole blocking layer may be selected according to the material of the adjacent electrode and material of the adjacent photoconducting layer 30. A material is preferably employed having an ionization potential (Ip) that is at least 1.3 eV more than the work function (Wf) of the material of the adjacent electrode, and an electron affinity (Ea) that is about the same as, or greater than, the Ea of the material of the photoconducting layer 30. Since there is explanation of details regarding applicable materials as such an electron acceptor organic material given in JP-A No. 2009-32854 further explanation thereof is omitted.

Note that the position of the electron blocking layer and the hole blocking layer may be reversed in cases in which there is a bias voltage set such that holes from charges generated in the photoconducting layer 30 move into the bias electrode 32, and electrons from the charges move into the collection electrode 34. The electron blocking layer and the hole blocking layer may both be provided, however a certain degree of dark current suppressing effect can be obtained as long as one or other thereof is provided.

Figure 6:
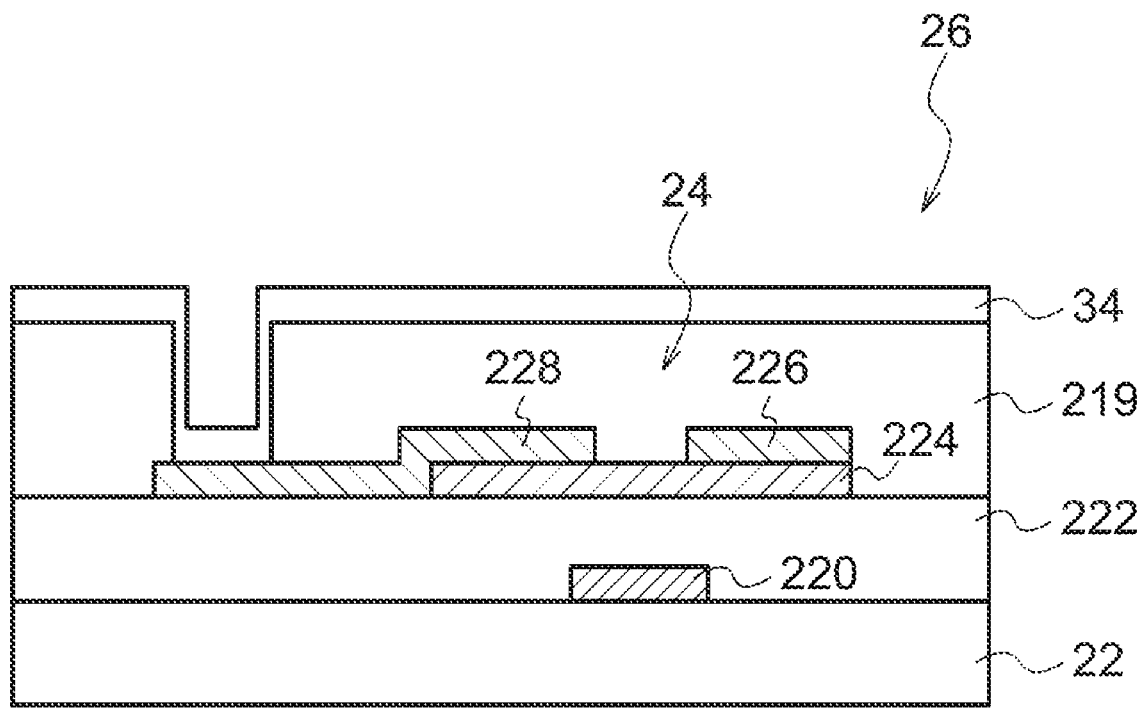
FIG. 6 is a cross-section schematically showing a configuration of a switch element of a radiation detector according to an exemplary embodiment.

FIG. 6 shows a schematic configuration of the switch element 24.

The switch elements 24 are formed corresponding to the collection electrodes 34, and charge that has moved into the collection electrode 34 is converted into an electrical signal and output by the switch elements 24. The region in which each of the switch elements 24 is formed has a portion that overlaps with the collection electrode 34 in plan view. By configuring thus, the switch elements 24 and the sensor portions 37 overlap along the thickness direction in each of the pixel portions. Note that in order to minimized the surface area of the radiation detection panel 20 (pixel portions) the regions formed with the switch elements 24 are preferably completely covered by the collection electrodes 34.

Each of the switch elements 24 is formed with stacked layers of a gate electrode 220, a gate insulation film 222, and an active layer (channel layer) 224, further formed with a source electrode 226 and a drain electrode 228 spaced apart by a specific amount and formed on the active layer 224.

The drain electrode 228 is electrical connected to the collection electrode 34 through a corresponding wiring line of an electrically conductive material formed so as to pass through an insulating layer 219 provided between the insulating substrate 22 and the collection electrode 34. Charge trapped by the collection electrode 34 can thereby be moved to the switch element 24.

The active layer 224 can be, for example, formed from amorphous silicon or a non-crystalline oxide, an organic semiconductor material, carbon nanotubes or the like. The material for configuring the active layer 224 is, however, not limited thereto.

Non-crystalline oxide materials capable of configuring the active layer 224 preferably include oxides including at least one of In, Ga, and/or Zn (for example In—O oxides), oxides including two or more of In, Ga, and/or Zn (such as In—Zn—O oxides, In—Ga—O oxides, Ga—Zn—O oxides) are more preferable, and oxides including In, Ga and Zn are particularly preferable. Preferable In—Ga—Zn—O oxides are non-crystalline oxides whose composition in a crystalline state would be represented by the formula $InGaO_3 (ZnO)_m$ (where m is a positive integer less than 6), and represented by $InGaZnO_4$ is more preferable. Note that possible non-crystalline oxides for configuring the active layer 224 are not limited thereto.

Possible organic semiconductor materials for configuring the active layer 224 included phthalocyanine compounds, pentacene, vanadyl phthalocyanine and the like, however there is no limitation thereto. Since explanation regarding details regarding structures of such phthalocyanine compounds is given in JP-A No. 2009-212389, further explanation is omitted.

By forming the active layer 224 of the switch elements 24 from a non-crystalline oxide or an organic semiconductor material formed with carbon nanotubes, since there is no absorption of radiation such as X-rays, or any absorption is restricted to an extremely small amount, noise generation in the switch elements 24 can be effectively suppressed.

When the active layer 224 is formed with carbon nanotubes, the switching speed of the switch elements 24 can be increased in speed, and the switch elements 24 can be formed having a low degree of absorption of light in the visible light region. Note that in cases in which the active layer 224 is formed with carbon nanotubes, since the performance of the switch elements 24 deteriorates significantly with incorporation of only a minute amount of metal impurity in the active layer 224, extremely high purity carbon nanotubes need to be separated or extracted, such as by centrifugal separation.

The above non-crystalline compounds, organic semiconductor materials, carbon nanotubes and organic photoelectric conversion materials are all capable of being formed into a film at low temperature. Accordingly, the insulating substrate 22 is not limited to a substrate with high heat resistance, such as a semiconductor substrate, a quartz substrate, a glass substrate or the like, and a flexible substrate, such as from a plastic, an aramid, or a bionanofiber substrate can be employed. Specifically, a flexible substrate from a polyester such as polyethylene terephthalate, polybutylene phthalate, polyethylene naphthalate or the like, polystyrene, polycarbonate, polyethersulphone, a polyarylate, a polyimide, a polycyclic olefin, a norbornene resin, a poly (chloro trifluouro ethylene) or the like, may be employed. By employing such a plastic flexible substrate, a reduction in weight can be achieved which is, for example, beneficial to portability.

Furthermore, for example, an insulation layer to ensure insulation ability, a gas barrier layer for preventing moisture and oxygen transmission, an undercoat layer for flattening and/or raising adhesiveness to the electrodes, or other layers may be provided to the insulating substrate 22.

Since an aramid can be used in high temperature process applications of 200° C. or above, a transparent electrode material can be high-temperature hardened to give a low resistance, and compatibility can also be made to automatic packaging of driver ICs including solder re-flow processes. Since an aramid has a thermal expansion coefficient that is close to that of indium tin oxide (ITO) and glass substrate, post manufacture warping is small, and it is not readily broken. An aramid can also be formed in a relatively thin substrate in comparison to a glass substrate. Note that the insulating substrate 22 may be formed with an aramid layered on an ultrathin glass substrate.

A bionanofiber composite is a composite of cellulose micro-fibril bundles (bacteria cellulose), produced by the bacterium Acetobacter Xylinum, and a transparent resin. The cellulose micro-fibril bundles are, with a width of 50 nm, a size that is 1/10 that of visible wavelengths, and have high strength, high elasticity, and low thermal expansion. By impregnating and hardening the bacteria cellulose in a transparent resin, such as, for example, an acrylic resin, an epoxy resin, or the like, a bionanofiber composite is obtained with a light transmissivity of 90% to light at 500 nm wavelength, while including fibers at a proportion of 60% to 70%. The bionanofiber composite has a low thermal expansion coefficient (3 to 7 ppm/K), comparable to that of crystalline silicon, strength comparable to steel (460 MPa), high elasticity (30 GPa) and is also flexible. This enables the insulating substrate 22 to be formed thinner in comparison to configuration with a glass substrate or the like.

In the present exemplary embodiment, the switch elements 24, the sensor portions 37 and the flattening layer 38 are formed in this sequence on the insulating substrate 22. The radiation detection panel 20 is formed by attaching the scintillator layer 28 above the insulating substrate 22 with the bonding layer 39 employing a bonding resin of low light absorption. The insulating substrate 22 formed up to a transparent insulating layer 206 is referred to below as the TFT substrate 26.

Figure 7:
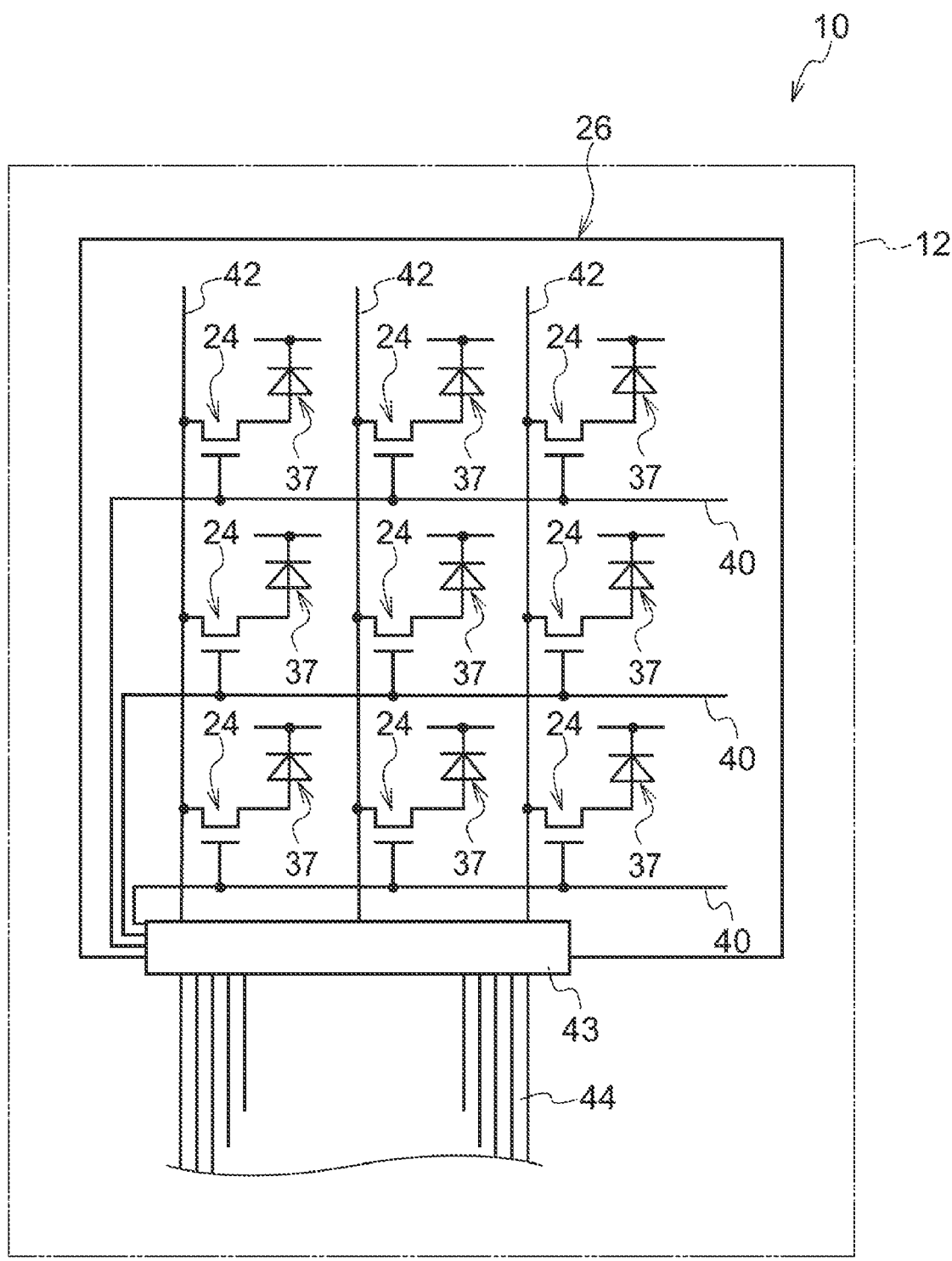
FIG. 7 is a circuit diagram showing a configuration of a radiation detection panel according to the present exemplary embodiment.

The sensor portions 37, as shown in FIG. 7, has the charge collection electrodes 34 disposed in a two-dimensional shape on the TFT substrate 26, with the switch elements 24 disposed corresponding thereto in a two-dimensional shape on the insulating substrate 22.

In the TFT substrate 26 are provided: plural gate lines 40 extending in a given direction (row direction) for switching each of the switch elements 24 ON or OFF; and plural data lines 42 extending in a direction orthogonal to the gate lines 40 (column direction) for reading out charge through the switch elements 24 that are in the ON state.

A flattening layer 38 is formed in the TFT substrate 26 for flattening above the TFT substrate 26. A bonding layer 39 is formed between the TFT substrate 26 and the scintillator layer 28 and above the flattening layer 38, for bonding the scintillator layer 28 to the TFT substrate 26.

The TFT substrate 26 is a quadrilateral shape in plan view, having 4 sides at the outside edges thereof. Specifically, the TFT substrate 26 is formed in a rectangular shape. A connection terminal 43 is disposed at one side of the peripheral edge of the TFT substrate 26 in plan view, connected to the individual gate lines 40 and the individual data lines 42. The connection terminal 43 is connected to the control section 50 through the connection wiring 44.

Figure 8:
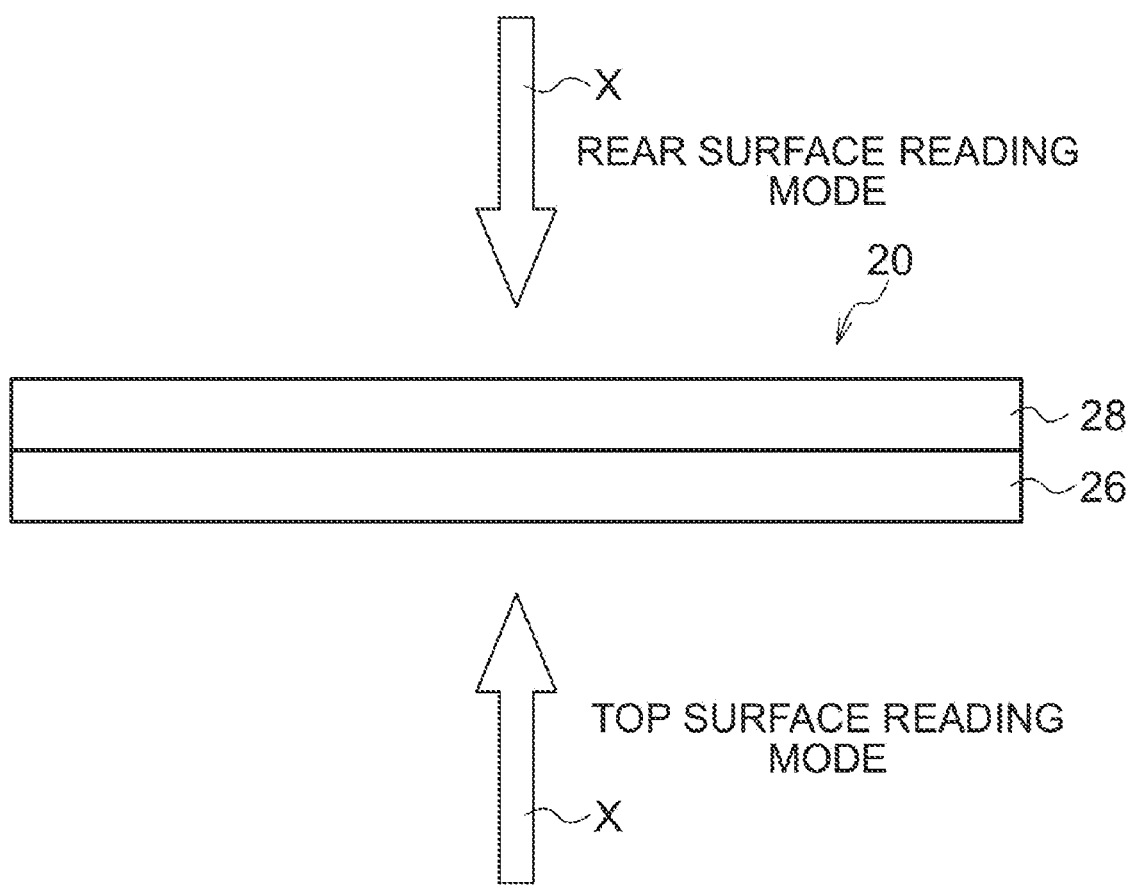
FIG. 8 is a cross-section for explaining a top surface reading mode and a rear surface reading mode of radiation onto a radiation detector.

As shown in FIG. 8, radiation may be irradiated from the front side of the radiation detection panel 20 where the scintillator layer 28 is bonded, or radiation may be irradiated from the TFT substrate 26 side (back side) of the radiation detection panel 20. When radiation is irradiated from the front side of the radiation detection panel 20, in a so-called Penetration Side Sampling (PSS) mode, there is more intense light generation at the top face side of the scintillator layer 28 (the opposite side to that of the TFT substrate 26). When radiation is irradiated from the back face side, in a so-called Irradiation Side Sampling (ISS) mode, the radiation that has passed through the TFT substrate 26 is irradiated onto the scintillator layer 28, and light generation is more intense at the TFT substrate 26 side of the scintillator layer 28. In each case charge is generated in each of the photoconducting layers 30 due to the light generated in the scintillator layer 28. Consequently, in the radiation detection panel 20, it is possible to design a higher sensitivity to radiation when radiation is irradiated from the front side than when radiation is irradiated from the back side, since radiation does not pass through the TFT substrate 26. The resolution of the radiographic images obtained is higher when radiation is irradiated from the back side than in cases in which radiation is irradiated from the front side, due to the light generation position in the scintillator layer 28 being closer to the photoconducting layers 30.

In the panel unit 12 according to the present exemplary embodiment, the radiation detection panel 20 is housed such that the scintillator layer 28 in the closed state, as shown in FIG. 3, is on the control unit 14 side, such that the TFT substrate 26 is on the outside (the opposite side to the control unit 14 side). The face on the outside in the closed state configures an irradiation face 18A (see also FIG. 1) employed in back face irradiation (ISS mode) for irradiating radiation of the radiation detection panel 20 from the back side. The face of the radiation detection panel 20 that faces the control unit 14 configures an irradiation face 18B (see also FIG. 2) employed in front face irradiation (PSS mode) for irradiation radiation of the radiation detection panel 20 from the front side.

In the radiation detection panel 20, there is substantially no radiation absorbed in the photoconducting layers 30 in configurations with an organic photoelectric conversion material as the photoconducting layers 30. Consequently, in the radiation detection panel 20 according to the present exemplary embodiment, since the radiation absorption amount by the photoconducting layers 30 is small even when the radiation passes through the TFT substrate 26 in ISS, a drop in the sensitivity to X-rays can be suppressed. In ISS, radiation passes through the TFT substrate 26 and reaches the scintillator layer 28, however, in cases in which the photoconducting layers 30 of the TFT substrate 26 are thus configured by an organic photoelectric conversion material, such a configuration is applicable to ISS since there is substantially no absorption of radiation by the photoconducting layers 30 and attenuation of radiation can be suppressed low.

It is possible to form both the non-crystalline oxide for configuring the active layer 224 of the switch element 24 and the organic photoelectric conversion material for configuring the photoconducting layers 30 into films at low temperature. Configuration may hence be made with the insulating substrate 22 formed with a plastic resin, aramid, or bionanofiber composite having low radiation absorption. Since the radiation absorption amount of the thus formed insulating substrate 22 is small, a fall off in the sensitivity to X-rays can be suppressed even when the radiation passes through the TFT substrate 26 in ISS.

Figure 9:
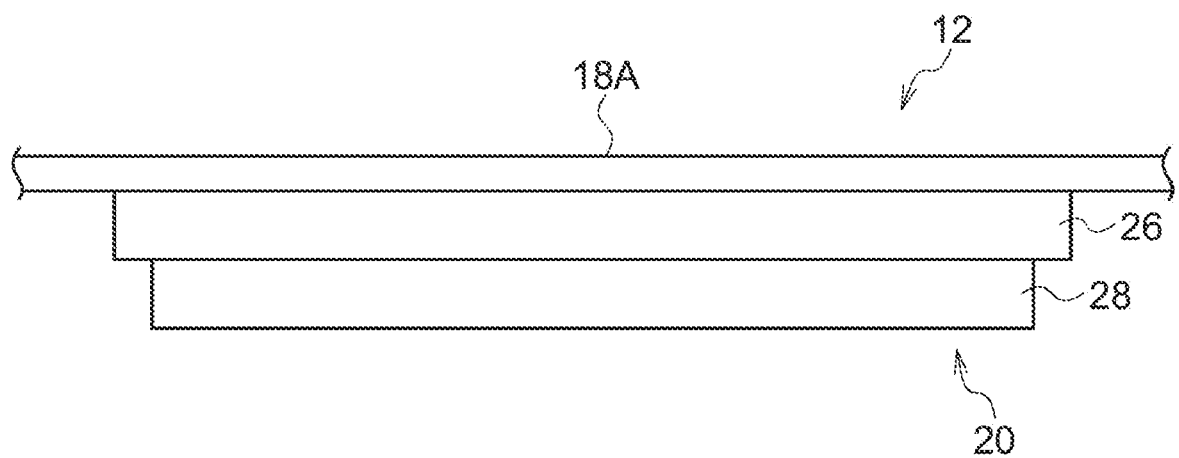
FIG. 9 is a cross-section showing an example of a configuration in which a radiation detection panel is disposed for a rear surface reading mode.

Accordingly, the radiation detection panel 20 may be one configured, as shown in FIG. 9, attached to a casing portion at the inside of the panel unit 12 such that the radiation detection panel 20 has the TFT substrate 26 on the irradiation face 18A side. In cases in which the insulating substrate 22 is formed from a plastic resin, aramid, or bionanofiber composite of high rigidity, the thickness of the casing of the panel unit 12 can be formed thinner due to the inherent rigidity of the radiation detection panel 20. In cases in which the insulating substrate 22 is formed from a plastic resin, aramid, or bionanofiber composite of high flexibility, the radiation detection panel 20 is not readily damaged when imparted with an impact due to inherent flexibility of the radiation detection panel 20.

Figure 10:
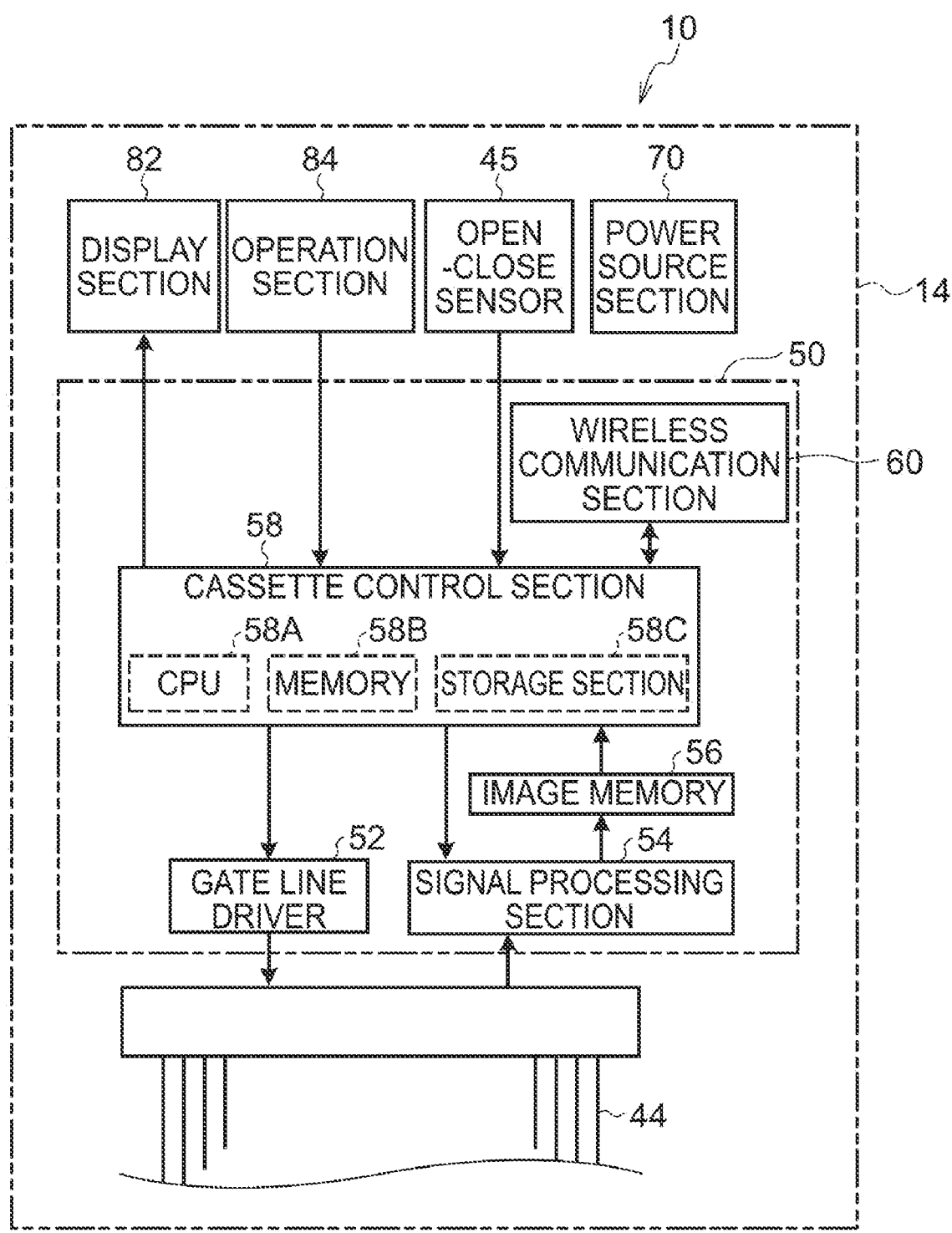
FIG. 10 is a block diagram showing a configuration of an electrical system of a control section according to the present exemplary embodiment.

FIG. 10 shows a block diagram of a schematic configuration of an electrical system of the control section 50 according to the present exemplary embodiment.

As shown in FIG. 10, the control section 50 is provided with: a gate line driver 52; a signal processing section 54; an image memory 56; a cassette control section 58 and a wireless communication section 60.

Each of the switch elements 24 (see also FIG. 5 and FIG. 7) are switched ON in sequence in row units by supplying a signal from the gate line driver 52 through the gate lines 40. The charge read out from the switch elements 24 that are in the ON state is transmitted as an electrical signal by the data lines 42 and input to the signal processing section 54. Accordingly, charge is read out in sequence in row units so as to enable a two-dimensional radiographic image to be acquired.

While not illustrated, the signal processing section 54 is provided for every individual data lines 42 with an amplification circuit for amplifying the input electrical signal and a sample and hold circuit. After the signal processing section 54 has amplified the electrical signal transmitted by the individual data lines 42, it holds the electrical signal in the sample and hold circuit. The output sides of the sample and hold circuits are connected in sequence to a multiplexer and an Analogue/Digital (A/D) converter, and the electrical signals held in the individual sample and hold circuits are input in sequence (serially) to the multiplexer so as to convert to digital image data using the A/D converter.

The image memory 56 is connected to the signal processing section 54 and image data that has been output from the A/D converter of the signal processing section 54 is stored in sequence in the image memory 56. The image memory 56 has storage capacity capable of storing a specific number of frames worth of image data, and every time radiographic image capture is performed, image data obtained by image capture is stored in sequence in the image memory 56.

The image memory 56 is connected to the cassette control section 58. The cassette control section 58 is configured by a microcomputer and is provided with a Central Processor Unit (CPU) 58A, a memory 58B including Read Only Memory (ROM) and Random Access Memory (RAM), and a nonvolatile storage section 58C configured from flash memory or the like. The cassette control section 58 controls operation of the electronic cassette 10 overall.

The wireless communication section 60 is connected to the cassette control section 58. The wireless communication section 60 conforms to a wireless Local Area Network (LAN) standard, as typified by the Institute of Electrical and Electronics Engineers (IEEE) standards 802.11a/b/g, and controls transmission of various data by wireless communication between to and from an external device. The cassette control section 58 is capable of wireless communication through the wireless communication section 60 with an external device for controlling radiographic image capture overall, such as, for example, a console, such that it is possible to transmit and receive various data to and from the console. The cassette control section 58 stores various data such as, for example, image capture conditions and patient data that has been received from the console through the wireless communication section 60, and starts reading out charge based on the image capture conditions.

The cassette control section 58 is connected to the display section 82, the operation section 84, and the open-close sensor 45, respectively, and controls display of various data on the display section 82. The cassette control section 58 can ascertain the contents of operation on the operation section 84 and the open or closed state of the panel unit 12 and the control unit 14.

The power source section 70 is provided, as mentioned above, in the electronic cassette 10, and each of the circuits and each of the elements described above (such as, for example, a micro computer that functions as the display section 82, the operation section 84, the open-close sensor 45, the gate line driver 52, the signal processing section 54, the image memory 56, the wireless communication section 60, and the cassette control section 58) are operated by power that has been supplied from the power source section 70. The power source section 70 has an internal battery installed (a rechargeable battery capable of recharging) so that the portability of the electronic cassette 10 is not compromised, and power is supplied from the charged battery to the various circuits and elements. Wiring connecting the power source section 70 to the various circuits and various elements is omitted in FIG. 10.

Explanation now follows regarding operation of the electronic cassette 10 according to the present exemplary embodiment.

The electronic cassette 10 is, as shown in FIG. 1 and FIG. 3, transported in the closed state with the panel unit 12 and the control unit 14 folded together and superimposed on each other.

In the electronic cassette 10, in order to capture a radiographic image, the panel unit 12 and the control unit 14 are side-by-side in the open state, as shown in FIG. 2. The electronic cassette 10 receives patient data from the console through the wireless communication section 60. When the patient data has been received, based on this patient data the cassette control section 58 controls such that data relating to the patient (for example, patient name and identification (ID)) is displayed on the display section 82. Since the electronic cassette 10 according to the present exemplary embodiment displays the name and ID on the display section 82, confirmation can be made as to whether or not there has been a mix up with the patient on whom imaging is going to be performed by, for example, the imaging technician ascertaining the name with the patient themselves, and comparing the ascertained name against the name displayed on the above screen.

The electronic cassette 10 according to the present exemplary embodiment is enabled for capturing still images in the closed state, and enabled for capturing video images in the open state.

Figure 11:
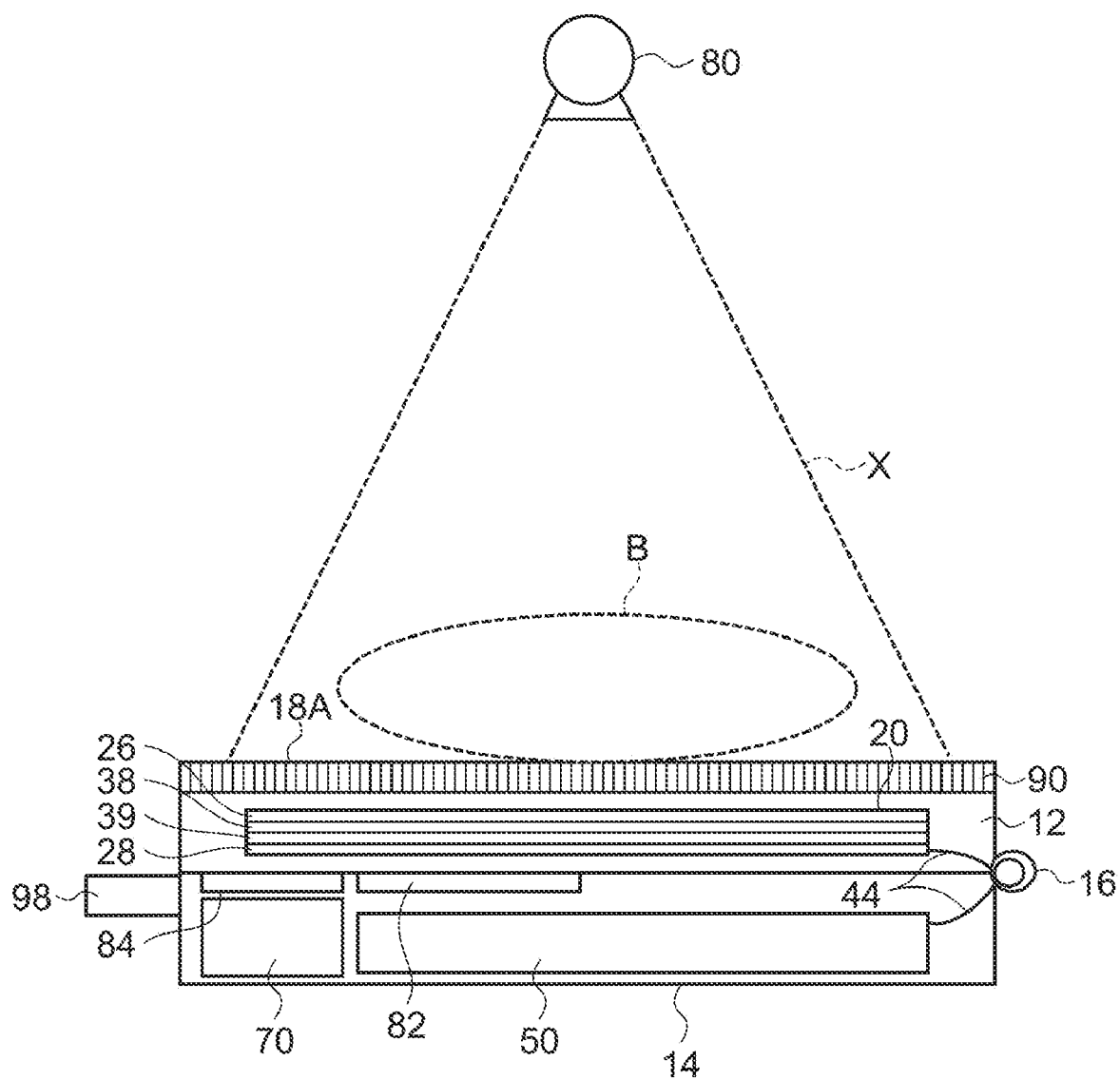
FIG. 11 is a cross-section showing disposed states of each portion of an electronic cassette according to the present exemplary embodiment when performing image capture in the closed state.
Figure 12:
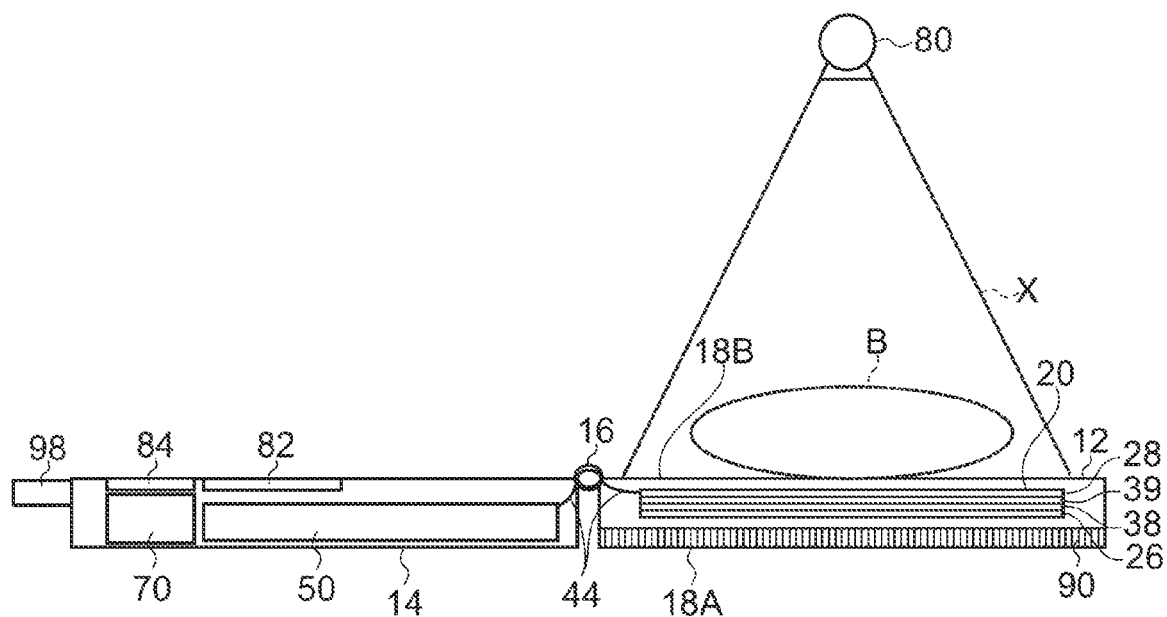
FIG. 12 is a cross-section showing disposed states of each portion of an electronic cassette according to the present exemplary embodiment when performing image capture in the open state.

After completing confirmation of the patient, in order to capture a still image the imaging technician disposes the electronic cassette 10 in the closed state as shown in FIG. 11 with a separation to a radiation generation device 80 that generates radiation, and disposes an imaging target location B on the patient above the irradiation face 18A. However, in order to capture a video image, the electronic cassette 10 is disposed in the open state as shown in FIG. 12 with a separation to the radiation generation device 80, and the imaging target location B of the patient is disposed over the irradiation face 18B.

The cassette control section 58 ascertains the open or closed state of the panel unit 12 and the control unit 14 based on the detection result with the open-close sensor 45, with a still image mode enabling a still image to be captured adopted when in the closed state, and a video image mode enabling a video image to be captured adopted when in the open state. The cassette control section 58 notifies the image capture mode to the console through the wireless communication section 60.

The console enables setting of image capture conditions according to the notified image capture mode and image capture conditions are set by the imaging technician. When setting of the image capture condition is completed, the console transmits image capture condition data expressing the set image capture conditions, by wireless communication to the electronic cassette 10.

After completing setting the image capture conditions, the imaging technician performs an instruction operation to the console to instruct image capture start. Accordingly, radiation of a radiation amount in accordance with the pre-allocated image capture conditions and the like is emitted from the radiation generation device 80. Radiation X emitted from the radiation generation device 80 passes through the imaging target location B, and after picking up and carrying image data thereby, the radiation X is irradiated onto the electronic cassette 10.

The radiation X irradiated from the radiation generation device 80 arrives at the electronic cassette 10 after it has passed through the imaging target location B. Accordingly, charge is collected and stored in each of the charge collection electrodes 34 of the radiation detection panel 20 installed in the electronic cassette 10 according to the radiation amount of the radiation X irradiated.

The cassette control section 58 controls the gate line driver 52 so as to output an ON signal from the gate line driver 52 to each of the gate lines 40 in sequence 1 line at a time, such that each of the switch elements 24 connected to each of the gate lines 40 are switched on in sequence 1 line at a time. Accordingly, the charge that has accumulated in the charge collection electrodes 34 flows out as an electrical signal to each of the data lines 42 in sequence 1 line at a time. The electrical signal flowing out of each of the data lines 42 is input to the signal processing section 54, converted into digital image data, and stored in the image memory 56.

For the still image capture mode, when 1 frames worth of image data has finished being read out, the cassette control section 58 ends reading out and transmits the image data stored in the image memory 56 to the console. For video image capture mode, the cassette control section 58 repeatedly reads out image data, and serially transmits the image data stored in the image memory 56 to the console.

The electronic cassette 10 according to the present exemplary embodiment houses the control section 50 and the power source section 70 which act as large heat sources in the control unit 14, and houses the radiation detection panel 20 in the panel unit 12, and rotatably connects one edge of each of the control unit 14 and the panel unit 12 through the hinge 16, such that two states are adopted, these being the closed state in which one face of the control unit 14 faces one face of the panel unit 12, and the open state in which the one face of the control unit 14 and the one face of the panel unit 12 are side by side and face in substantially the same direction. Consequently, as a result of being able to weaken thermal coupling of the control section 50 and the power source section 70 to the radiation detection panel 20, rise in temperature of the radiation detection panel 20 can be suppressed.

In the electronic cassette 10 according to the present exemplary embodiment, when in the open state, the bottom face of the panel unit 12 is positioned higher than the bottom face of the control unit 14. However, in this state, since the support member 90 that supports the panel unit 12 is placed below the bottom face of the panel unit 12, this results in being able to prevent distortion of the panel unit 12, and hence deterioration of captured image quality and breakage of the panel unit 12 caused by distortion of the panel unit 12 can be prevented. In particular, in the electronic cassette 10 according to the present exemplary embodiment, since the panel unit 12 has a thickness that is thinner than that of the control unit 14, the effect of preventing damage of the radiation detection panel 20 can be exhibited at an even higher level.

In the electronic cassette 10 according to the present exemplary embodiment, when in the open state, the top face of the control unit 14 and the top face of the panel unit 12 are configured so as to be at substantially the same height as each other. Accordingly, when performing image capture in a state in which the investigation subject is placed on the electronic cassette 10, problems arising from a difference in level between one face of the control unit 14 and one face of the panel unit 12 can be prevented from occurring.

In the electronic cassette 10 according to the present exemplary embodiment, since application is made of a member having the grid 90A for removing scattered rays of radiation due to the image capture subject during image capture, scattered rays of radiation due to the investigation subject during image capture can be removed.

In the electronic cassette 10 according to the present exemplary embodiment, since the radiation detection panel 20 is capable of detecting by irradiation from both the front face and the back face, radiographic image capture can be performed in either state out of the closed state and the open state.

In the electronic cassette 10 according to the present exemplary embodiment, the open-close sensor 45 is provided for detecting which state out of the closed state and the open state the control unit 14 and the panel unit 12 are in, control is performed by the control section 50 such that still image capture is performed when the closed state is detected by the open-close sensor 45, and control is performed such that video image capture is performed when the open state is detected by the open-close sensor 45. Accordingly, this results in being able to perform image capture with the panel unit 12 and the control unit 14 in a superimposed state during still image capture, such that breakage of the radiation detection panel 20 can be prevented. It also results in being able to increase the surface area during video image capture, such that the heat dissipation effect can be enhanced for video image capture, where heat generation is higher than during still image capture.

In particular, in the electronic cassette 10 according to the present exemplary embodiment, by performing video image capture in the open state during video image capture having a large amount of heat generation, heat that has been generated by the control section 50 in the control unit 14 can be suppressed from transmission to the radiation detection panel 20 in the panel unit 12, and changes to the characteristics of the radiation detection panel 20 are suppressed, stabilizing the quality of captured radiographic images, and also raising the durability of the radiation detection panel 20. The panel unit 12 makes contact with the patient during radiographic image capture, however by suppressing the heat generated by the control section 50 from transmission to the panel unit 12, the surface temperature of the panel unit 12 can be prevented from rising too high and causing discomfort to the patient. Furthermore, the radiation detection panel 20 is of a layered structure, with the materials configuring each of the layers having different thermal expansion coefficients from each other, and deformation and damage from heat due to this configuration can be suppressed, together and deterioration and delamination due to thermal cycling of the bonding member can also be suppressed.

In the electronic cassette 10 according to the present exemplary embodiment, by adopting the open state, due to the surface area increasing, the heat dissipation effect is enhanced. In particular, due to the large amount of heat generated during video image capture, preferably the surface area is increased at such times from the perspective of heat dissipation.

Furthermore, whereas there is substantially no change in sensitivity with changes in temperature for GOS, the sensitivity of CsI changes with an increase in temperature (for example, the sensitivity falls by about 0.3% for each 1° C. rise in temperature). Accordingly, when the scintillator layer 28 is formed with CsI, there is a large change in sensitivity of the scintillator layer 28 if the temperature of the scintillator layer 28 fluctuates widely during video imaging (fluoroscopic imaging) with continuous repeated image capture. This leads to large differences in density between the images of the first frames and the images of the final frames in a single cycle of video captured images, reduced legibility, and reducing diagnostic precision. However, with the electronic cassette 10 according to the present invention, heat generated in the control section 50 is not readily transmitted to the radiation detection panel 20 due to performing video imaging in the open state, and hence changes in sensitivity due to temperature changes in CsI can be suppressed.

In the electronic cassette 10 according to the present exemplary embodiment, configuration may be made such that still image capture is performed during video image capture in the open state. In such cases, since the electronic cassette 10 performs still image capture in the open state by performing still image capture during video image capture in the open state, the legibility of still images can be ensured even when appropriate image capture of plural still images is performed during video image capture.

In the electronic cassette 10 according to the present exemplary embodiment, since the operation section 84 and the display section 82 are present on the face of the control unit 14 that faces the front face of the panel unit 12 in the closed state, the operation section 84 and the display section 82 can both be protected when in the closed state, and also unintended operation of the operation section 84 can be prevented.

In the electronic cassette 10 according to the present exemplary embodiment, by performing still image capture in the closed state, due radiation being irradiated to the radiation detection panel 20 from the back side, this being the irradiation face 18A, radiographic images with high resolution can be obtained. In the electronic cassette 10 according to the present exemplary embodiment, by performing video image capture in the open state, due to radiation being irradiated to the radiation detection panel 20 from the front side, this being the irradiation face 18B, the sensitivity of the radiation detection panel 20 to radiation is raised, and so the radiation dose for irradiation during image capture can be suppressed lower, and radiation exposure of the imaging target location can be suppressed lower.

In the electronic cassette 10 according to the present exemplary embodiment, the wireless communication section 60 is provided within the control unit 14 so as to be separated from the patient when in the open state, and since an antenna employed in wireless communication is also separated from the patient, transmission interference does not readily occur.

While the present invention has been explained by way of the exemplary embodiments, the technical scope of the present invention is not limited to the scope of the above exemplary embodiments. Various changes and improvement can be made to the above exemplary embodiments within a scope not departing from the spirit of the invention, and the technical scope of the present invention also includes such changed and improved embodiments.

The above exemplary embodiments do not limit the invention according to the claims, and all of the combination of features explained in the exemplary embodiments above are not necessarily essential to the solution of the present invention. A number of configuration elements from out of the total configuration elements shown in the exemplary embodiments may be removed, and as long as an effect is obtained, the configuration from which a number of configuration elements have been removed is derivable as the invention.

For example, while explanation has been given in the above exemplary embodiments of cases in which the control unit 14 is a flat plate shape, the present invention is not limited thereto. For example, the radiation detection panel 20 can be formed from a glass substrate similar to that of a liquid crystal display, and made comparatively thin. However, in the control section 50, circuit elements, such as an inductance circuit, coil, or the like are provided, and often these circuit elements and a battery have a height that is relatively high compared to the radiation detection panel 20.

Figure 13:
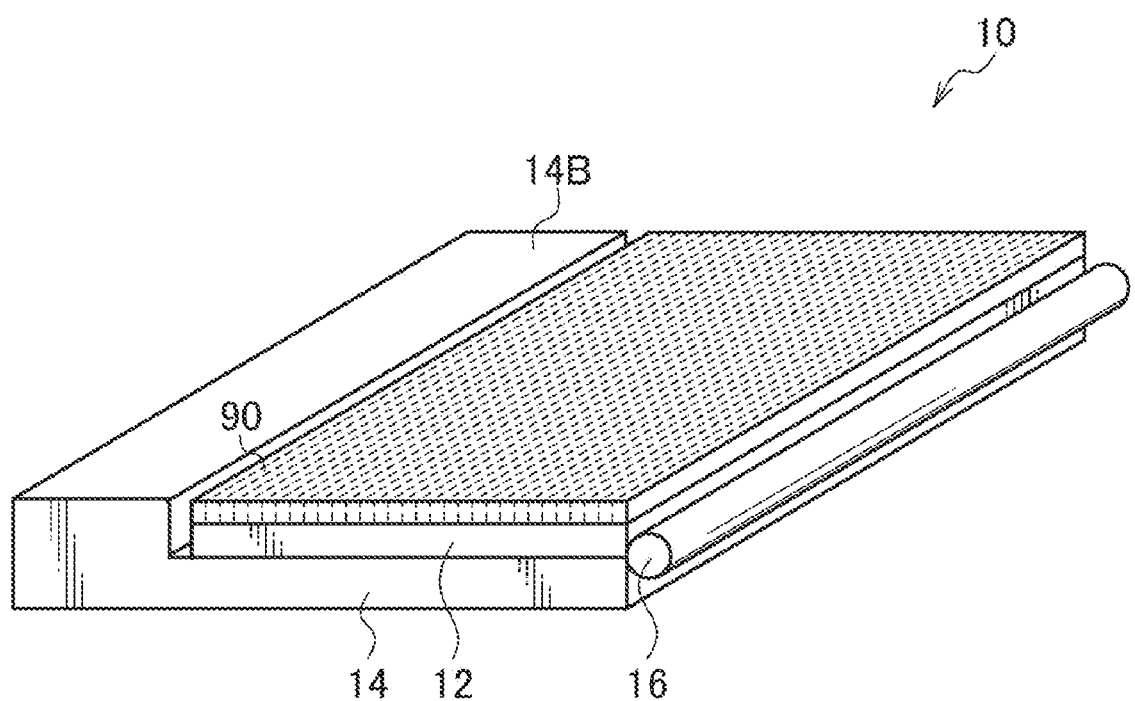
FIG. 13 is a perspective view showing a configuration of an electronic cassette according to another exemplary embodiment (in the closed state)
Figure 14:
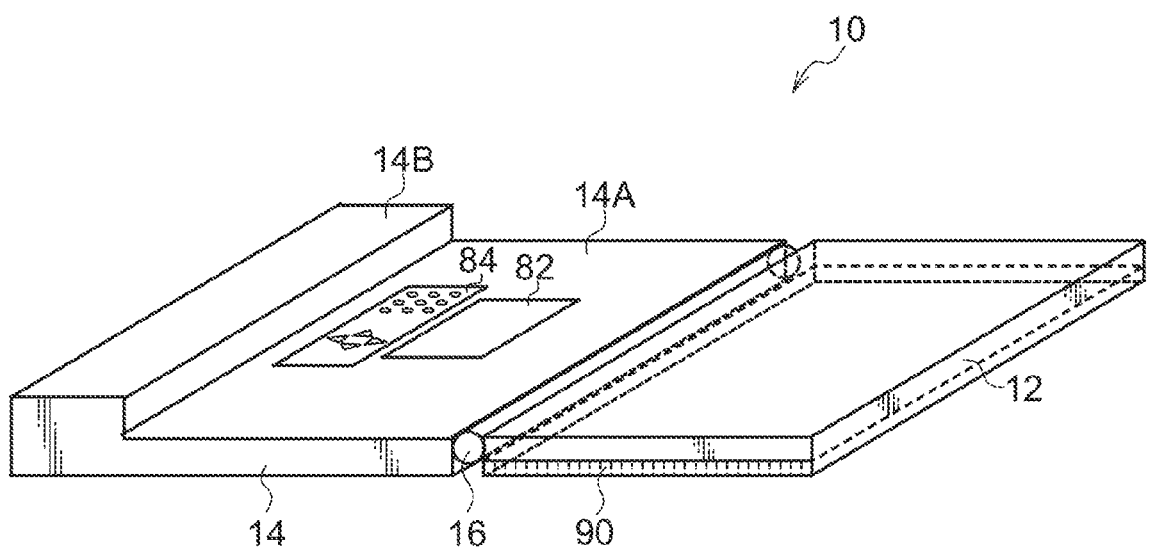
FIG. 14 is a perspective view showing a configuration of an electronic cassette according to another exemplary embodiment (in the open state)

As shown in FIG. 13 and FIG. 14, configuration may be made such that the electronic cassette 10 according to the above exemplary embodiments is formed with a thin panel unit 12, and the control unit 14 is formed with a superimposed portion 14A onto which the panel unit 12 and the support member 90 are folded over when in the closed state, and a non-superimposed portion 14B formed thicker than the superimposed portion 14A and not superimposed by the panel unit 12 and the support member 90. The thickness of the non-superimposed portion 14B is the same as the combined thickness of the superimposed portion 14A, the panel unit 12 and the support member 90. Configuration may then be made such that circuit elements such as the inductance circuit, coil, and the battery and the like are disposed within the non-superimposed portion 14B. In such cases, the display section 82 and the operation section 84 may be provided in the superimposed portion 14A, as shown in FIG. 14, or may be provided in the non-superimposed portion 14B. In such cases, a handle may be provided similarly to the example shown in FIG. 2, on the side face of the non-superimposed portion 14B, at the opposite side to the side on which the hinge 16 is provided.

In the above exemplary embodiment, explanation has been given of cases where wireless communication is performed to and from an external device, such as the console, however, the present invention is not limited thereto, and wired communication may be performed. In such cases too, by providing a connector for connecting a cable for performing wired communication on the control unit 14, the connector and the cable do not get in the way of the patient. When sliding the cassette under the investigation subject, since frictional resistance and excessive load is not incurred, problems due to poor connection, such as loose connection, broken wires or the like, can be made to not readily occur.

In the electronic cassette 10 according to the present exemplary embodiment, explanation has been given regarding cases of adopting the video image capture mode when in the open state, however the present invention is not limited thereto. For example, configuration may be made so as to accept still image capture image capture instructions from the operation section 84 even when in the open state, such that the cassette control section 58 operates the still image capture mode even in the open state when a still image capture image capture instruction has been received through the operation section 84.

Furthermore, in a modified example, configuration may be made such that while image capture is being performed in the video image capture mode in the open state, switching over to performing image capture in the still image capture mode can be made by accepting a still image capture instruction or the like.

While not particularly mentioned in the above exemplary embodiments, any gap between the inside wall of the panel unit 12 on the radiation irradiation face side in the closed state and the radiation detection panel 20 is preferably made as narrow as possible. This results in the distance between the imaging subject and the radiation detection panel 20 being shorter, blurring of images can be suppressed, and this is beneficial from the perspective of the quality of the images obtained by image capture.

In the above exemplary embodiment, explanation has been given of cases in which data relating to the patient is displayed by the display section 82, however the present invention is not limited thereto. For example, a captured radiographic image or image capture conditions may be displayed by the display section 82. In cases such as when the same imaging target location on the patient is periodically imaged over a period of time to observe any changes, configuration may be made such that a radiographic image of the imaging target location of the patient that was captured previously is received from the console, so as to display this radiographic image with the display section 82. A sample image according to the imaging target location or imaging guidance may also be displayed on the display section 82.

Figure 15:
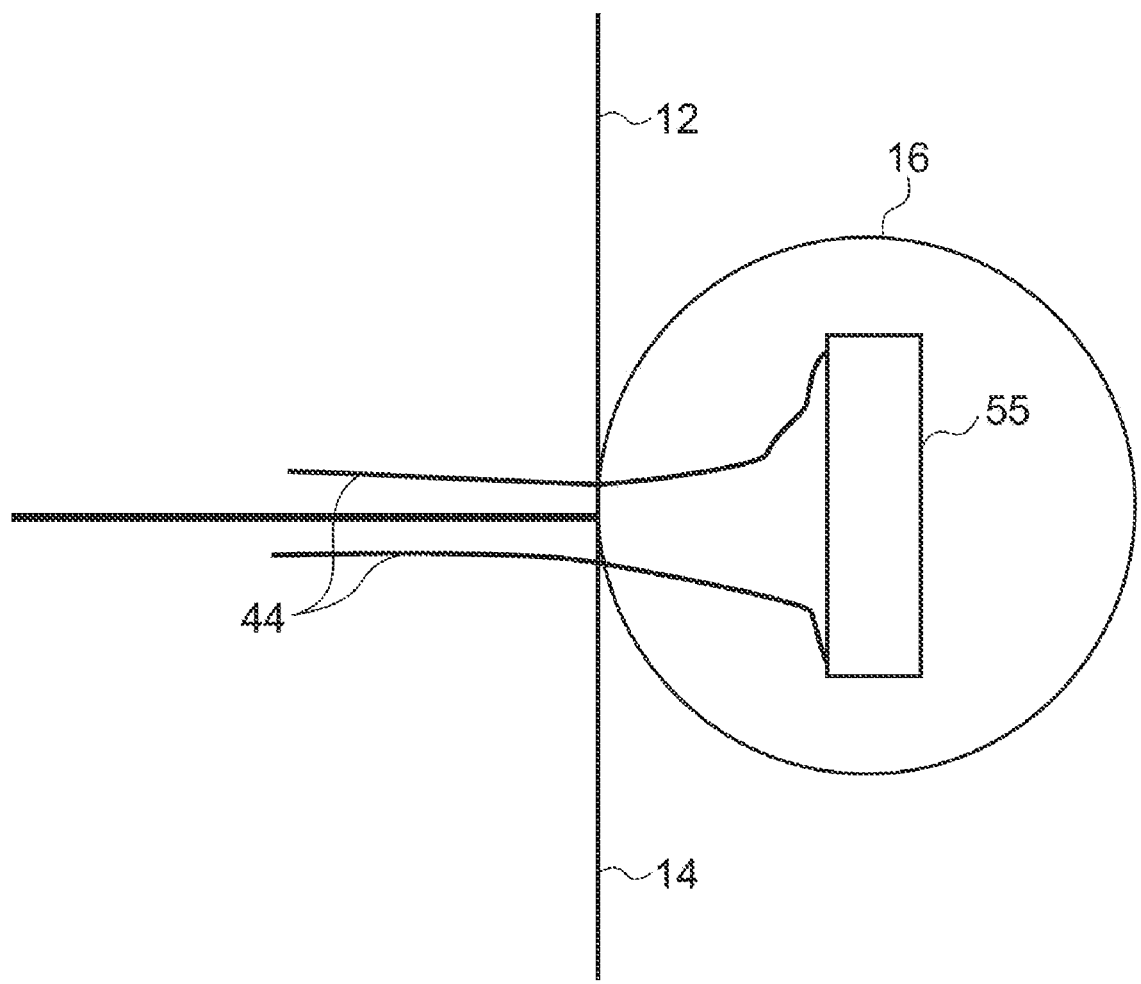
FIG. 15 is a cross-section showing a configuration in which an integrated circuit is provided inside a hinge in an electronic cassette according to another exemplary embodiment.
Figure 16:
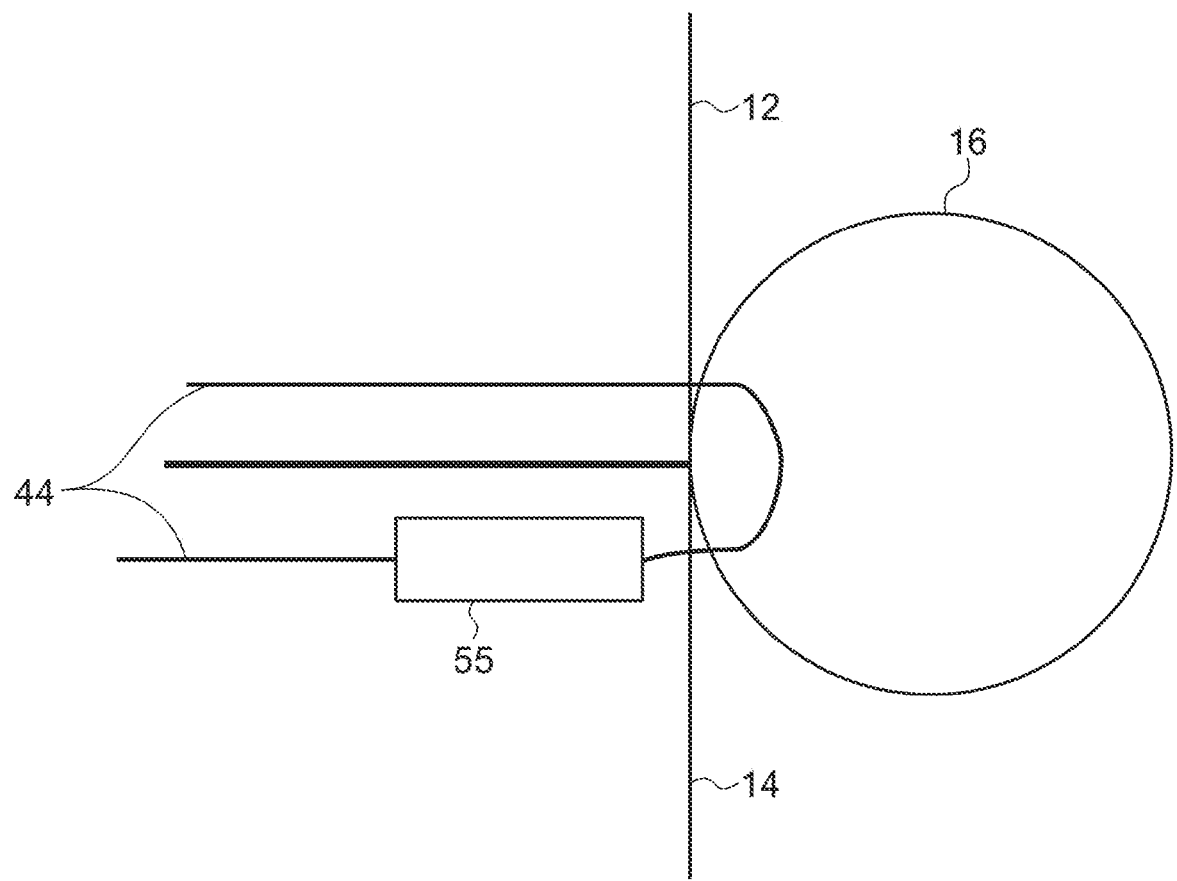
FIG. 16 is a cross-section showing a configuration in which an integrated circuit is provided in the vicinity of a hinge in an electronic cassette according to another exemplary embodiment.
Figure 17:
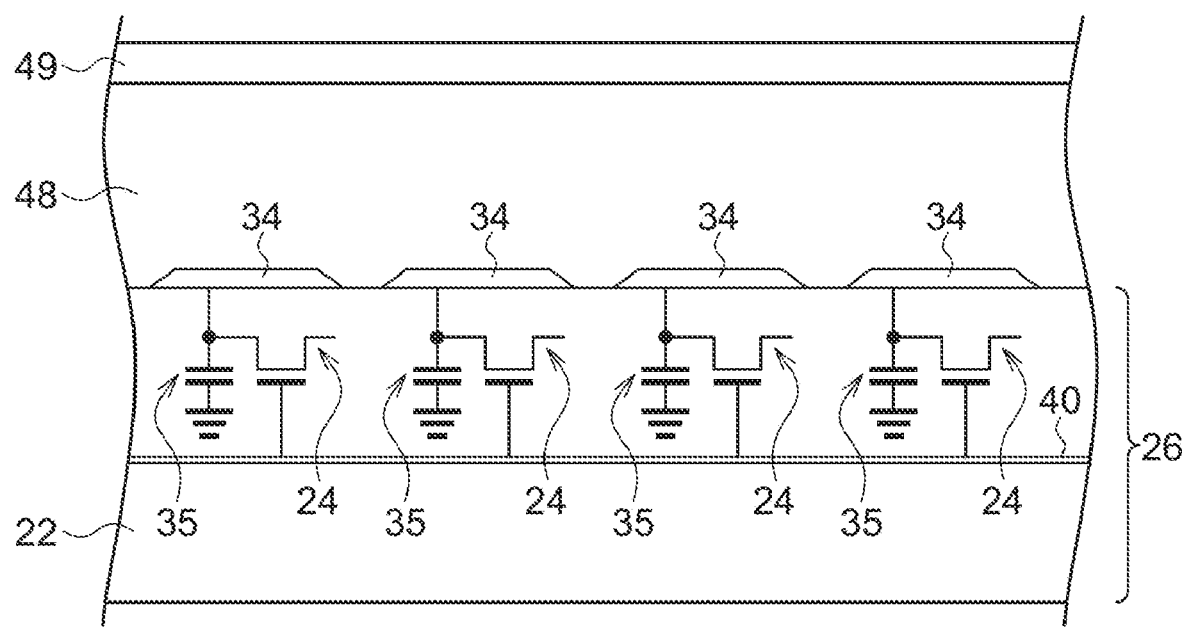
FIG. 17 is a cross-section showing a configuration of a direct conversion type of radiation detection panel according to another exemplary embodiment.

In the above exemplary embodiments, explanation has been given of a case in which the gate line driver 52 and the signal processing section 54 are provided within the control unit 14, however the present invention is not limited thereto. For example, electronic components such as the gate line driver 52, the signal processing section 54, and the like may be configured with an integrated circuit 55, such as an Application Specific Integrated Circuit (ASIC), as shown by an example in FIG. 15, with the integrated circuit 55 disposed within the hinge 16. Due thereto, the cooling effect on the integrated circuit 55 can be enhanced. The integrated circuit 55 is not necessarily provided within the hinge 16, and as shown in an example in FIG. 16, may be provided to the control unit 14 in the vicinity of the hinge 16, or provided to the panel unit 12 in the vicinity of the hinge 16.

In such cases, obviously electronic circuits provided in the signal processing section 54, such as the amplification circuit, the sample and hold circuit, the multiplexer, the A/D converter and the like, need not necessarily be configured in a single integrated circuit, some of these electronic circuits may be configured separately to the integrated circuit, and these electronic circuits may be provided in a different position to that of the integrated circuit.

Configuration may be made such that the state of the electronic cassette 10, such as power ON/OFF, transition from sleep mode to image capture mode and the like, automatically transition according to opening or closing of the control unit 14 and the panel unit 12.

In the above exemplary embodiments, explanation has been given, as an example of a radiation detection panel according to the present invention, of cases in which the indirection conversion type radiation detection panel 20 is applied, wherein radiation is first converted into light in the scintillator layer 28 and then the converted light is further converted into charge by the photoconducting layers 30 and accumulated. However, the present invention is not limited thereto, and configuration may be made, for example, employing a direct conversion type radiation detection panel in which radiation is directly converted into charge by a sensor section, using amorphous selenium or the like.

An example of a direction conversion type radiation detection panel is shown in FIG. 14. In this radiation detection panel, a photoconducting layer 48 that converts irradiated radiation into charge is formed over the TFT substrate 26. One or more of the following chemical compounds may be employed as a principal component for the photoconducting layer 48: amorphous Se, $Bi_{12}MO_{20}$ (M:Ti, Si, Ge), $Bi_4M_3O_{12}$ (M:Ti, Si, Ge), $Bi_2O_3$, $BiMO_4$ (M: Nb, Ta, V), $Bi_2WO_6$, $Bi_{24}B_2O_{39}$, ZnO, ZnS, ZnSe, ZnTe, $MNbO_3$ (M: Li, Na, K), PbO, $HgI_2$, $PbI_2$, CdS, CdSe, CdTe, $BiI_3$, GaAs, and the like. However, a non-crystalline (amorphous) material with high dark-resistance, showing good photoconductivity to X-ray radiation, and capable of forming a film of large surface area at a low temperature using a vacuum deposition method is preferable. A bias electrode 49 is formed on the photoconducting layer 48 on the surface on the side of the photoconducting layer 48, in order to apply a bias voltage to the photoconducting layer 48. In the TFT substrate 26, similarly to with an indirect conversion type radiation detection panel, charge collection electrodes 34 are formed to collect the charge that has been generated in the photoconducting layer 48. In the TFT substrate 26 of the direct conversion type radiation detection panel, charge storage capacitors 35 are provided for accumulating charge that has been collected by each of the charge collection electrodes 34. The charge accumulated by each of the charge storage capacitors 35 is read by switching on the switch elements 24.

Figure 18:
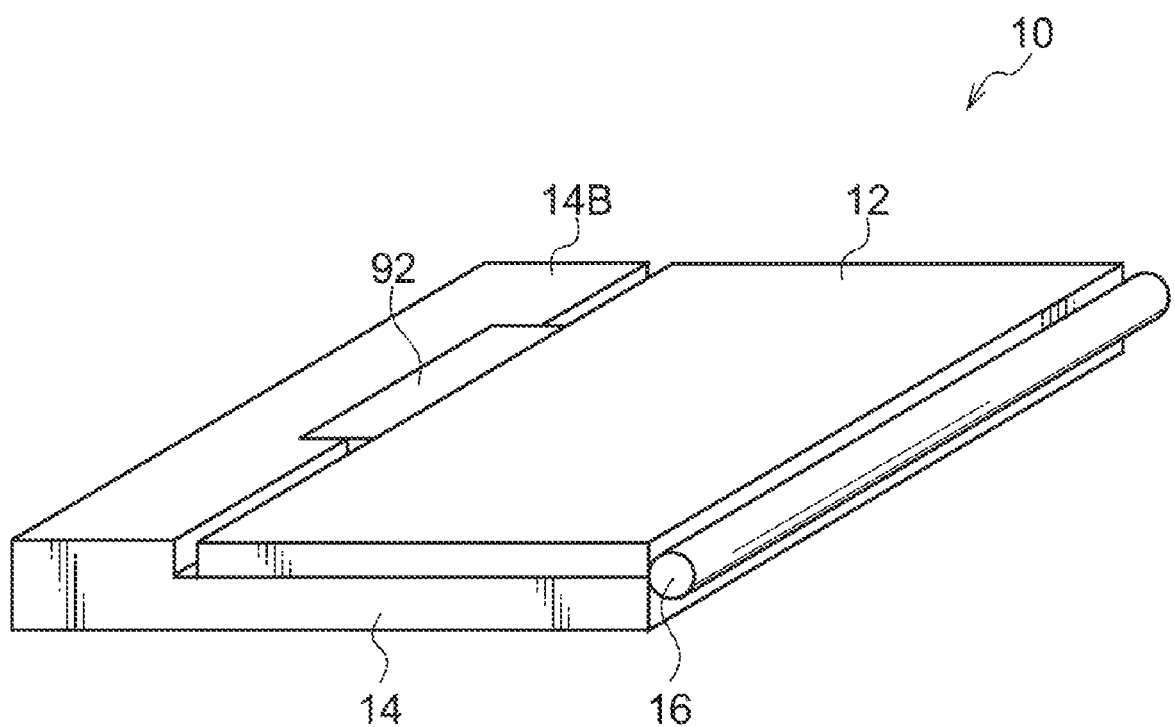
FIG. 18 is a perspective view showing a configuration of an electronic cassette according to another exemplary embodiment (in the closed state)
Figure 19:
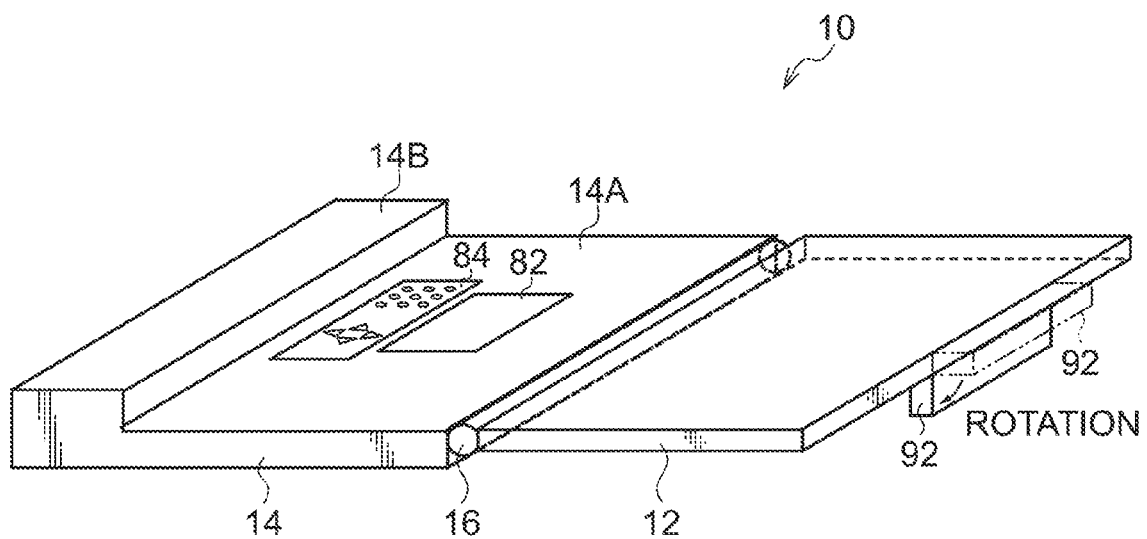
FIG. 19 is a perspective view showing a configuration of an electronic cassette according to another exemplary embodiment (in the open state)

While explanation has been given in the above exemplary embodiments of cases in which the support member 90 housing the grid 90A is applied as the support member of the present invention, the present invention is not limited thereto. As shown in the examples in FIG. 18 and FIG. 19, configuration may be made in which a displaceable support member 92 is applied as the support member of the present invention, such that when in the closed state, the support member 92 is inset in the control unit 14, and when in the open state, is positioned below the bottom face of the panel unit 12. In such a case, the portability of the electronic cassette 10 can be enhanced in comparison to application of the support member 90.

Figure 21:
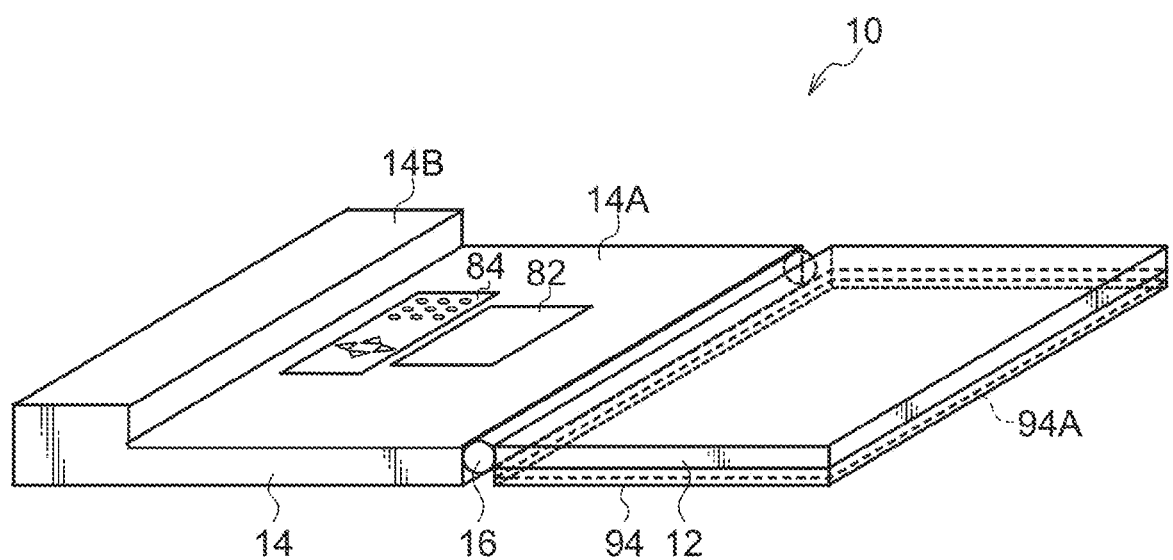
FIG. 21 is a perspective view showing a configuration of an electronic cassette according to another exemplary embodiment (in the open state)
Figure 22:
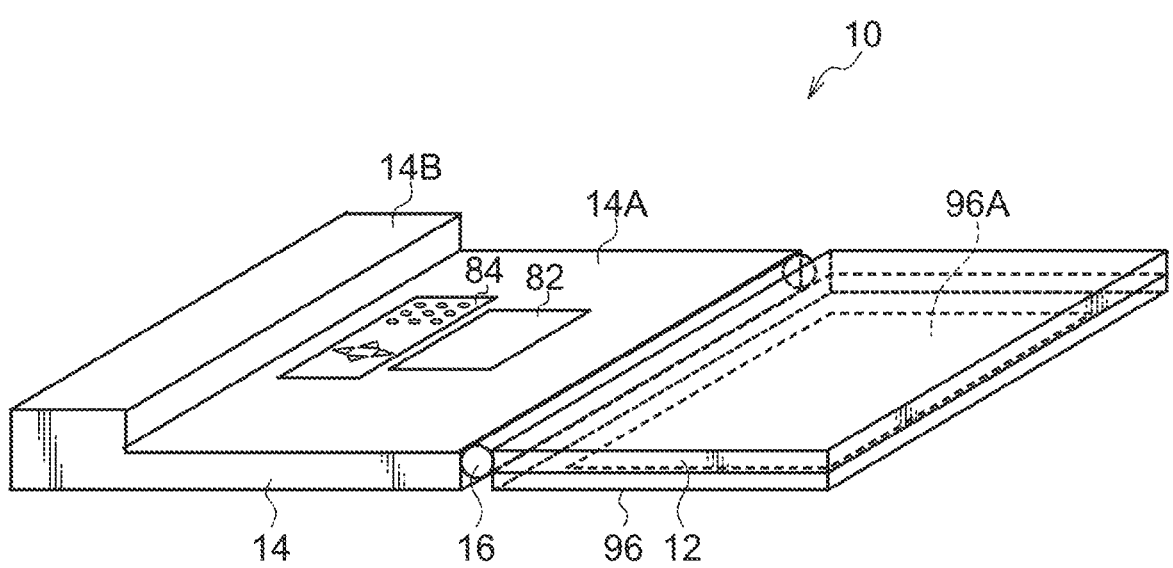
FIG. 22 is a perspective view showing a configuration of an electronic cassette according to another exemplary embodiment (in the open state)

Similarly, as shown in the example in FIG. 21, configuration may be made in which a support member 94 having metal 94A for preventing back scattering during image capture is applied as the support member of the present invention, and configuration may also be made in which a support member 96 having an attachable-detachable configured sheet-shaped battery 96A is applied as the support member of the present invention, as shown in the example in FIG. 22. As a modified example of the support member 96, a cooling gel sheet (not shown in the drawings) for cooling the 96A may be provided in the vicinity of the battery 96A. In cases in which the support member 96 is applied, the battery 96A may be employed in place of the battery provided to the power source section 70, or may be used in combination therewith.

The metal may include, lead, tungsten, tantalum, barium sulfate, and the like.

In the examples shown in FIG. 21 and FIG. 22, the support member 94 or the support member 96 are of substantially the same shape and dimensions in plan view as the panel unit 12, and the thickness is substantially the same as the height from the bottom face of the panel unit 12 to the bottom face of the control unit 14 when in the open state, namely the distance in the vertical direction to the placement surface of the electronic cassette 10. The role for supporting the panel unit 12 in the open state is similar to that of the support member 90.

Figure 20:
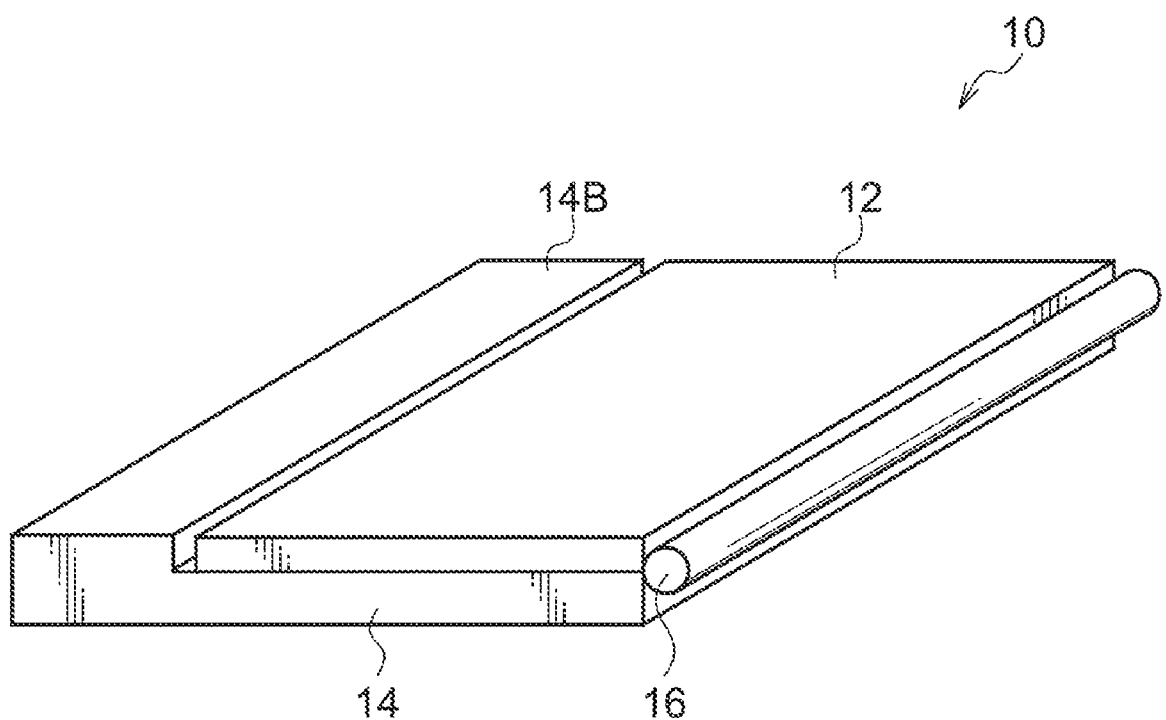
FIG. 20 is a perspective view showing a configuration of an electronic cassette according to another exemplary embodiment (in the closed state)

In such cases, the support member 94 or the support member 96 may be in a bonded state to the panel unit 12 using a bonding agent, or, due to the comparatively heavy lead and battery, may be configured so as to be attracted by magnetic force, fitted through a fitting member, or the like. Preferably the support member 94 or the support member 96 is made attachable to and detachable from the panel unit 12, and the support member 94 or the support member 96 removed when in the closed state, as in the example shown in FIG. 20. In particular, when the support member 94 is applied, it is necessary to remove the support member 94 when performing image capture in the closed state since otherwise the support member 94 would attenuate the radiation.

Figure 23:
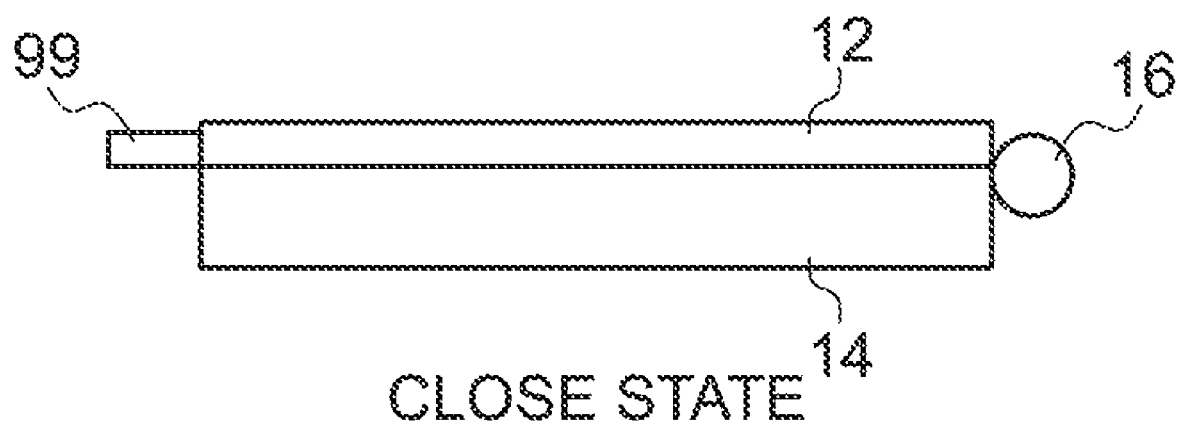
FIG. 23 is a perspective view showing a configuration of an electronic cassette according to another exemplary embodiment (in the closed state)
Figure 24:
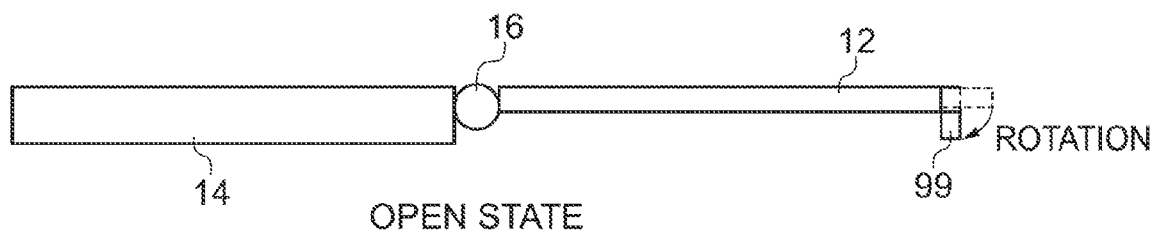
FIG. 24 is a perspective view showing a configuration of an electronic cassette according to another exemplary embodiment (in the open state)

Furthermore, as the support member of the present invention, as shown in the example in FIG. 23 and FIG. 24, configuration may be made in which a dual purpose member 99 is applied, functioning as a handle when protruding out from the side of the electronic cassette 10 in the closed state, and, by being displaceably configured, functioning as a support member positioned below the bottom face of the panel unit 12 when in the open state. In such cases too, the portability of the electronic cassette 10 can be enhanced in comparison to cases in which the support member 90 is applied.

While explanation has been given in the above exemplary embodiments of cases in which the radiation detection panel 20 capable of image capture from both sides, the front face and the back face, is applied as the radiation detection panel of the present invention, the present invention is not limited thereto. Configuration may be made in which a radiation detection panel only capable of image capture from one side is applied.

In cases in which the support member 90 installed with the grid 90A is employed, by configuring with either a two-face image capture capable radiation detection panel or a single-face image capture capable radiation detection panel applied as the radiation detection panel, the examples can be given as modes of use of the support member 90.

Namely, in cases in which a single-face image capture capable radiation detection panel is applied, image capture in the open state is by placing an imaging subject thereon. When image capture is performed in such a case employing a grid, the support member 90 is removed from the panel unit 12, and image capture is performed with the imaging subject placed on the panel unit 12. However, in such a case, since the bottom face of the panel unit 12 needs to be supported by a member other than the support member 90, application is made of another support member, such as the support member 92 shown in FIG. 19, the dual purpose member 99 shown in FIG. 24, or the like, in place of the support member 90. Note that in such cases, the support member such as the support member 92, the dual purpose member 99 and the like can be formed so as to integrally hold the support member 90 to the panel unit 12, and ease of use can be enhanced.

In contrast, when a two-face image capture capable radiation detection panel is applied in the electronic cassette 10 according to the above exemplary embodiments, in order to perform image capture using a grid, image capture is performed in the closed state, and in order to perform image capture without using a grid, image capture is performed in the open state. Consequently, image capture can be performed without having to detach or attach the support member 90.

Figure 25:
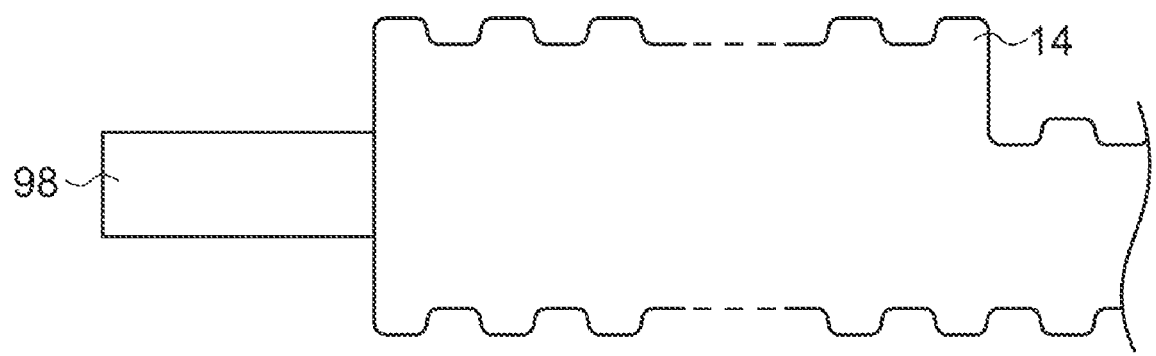
FIG. 25 is a side view showing a profile of a surface of a control unit of an electronic cassette according to another exemplary embodiment.

In the above exemplary embodiment, explanation has been given regarding cases in which the surface of the control unit 14 is flat, however the present invention is not limited thereto. For example, as shown in an example in FIG. 25, the surface of the control unit 14 may be formed in an undulating shape. In such cases, this results in being able to increase the surface area of the control unit 14, and the heat dissipation effect can be enhanced. Note that obviously the undulating shape in such a case may be the wave pattern shown in FIG. 25, or another shape such as a semi-circular shape, rectangular shape or the like.

In the above exemplary embodiment, explanation has been give of cases in which the hinge 16 is applied as a connecting member of the present invention, however the present invention is not limited thereto. Any other member is applicable thereto as long as it is capable of rotatably connecting together the control unit 14 and the panel unit 12.

While explanation has been given in the above exemplary embodiments of cases in which the support member 90 housing the grid 90A is applied as the support member of the present invention, the present invention is not limited thereto. The grid 90A may be applied as the support member of the present invention on its own. In such cases, similarly to the above exemplary embodiments, the grid 90A may be directly bonded to the panel unit 12 with a bonding agent, attracted by magnetic force, fitted through a fitting or the like.

In the above exemplary embodiments, explanation has been given of cases in which the display section 82 and the operation section 84 are both provided to the control unit 14, however the present invention is not limited thereto. Configuration may be made in which only one or other of the display section 82 or the operation section 84 is provided to the control unit 14.

The configurations of the electronic cassette 10 and the radiation detection panel 20 in the exemplary embodiments explained above are only examples, and obviously appropriate changes are possible within a scope not departing from the spirit of the present invention.

What is claimed is:

1. A radiographic imaging apparatus comprising:
   a control unit housing a control section and a power source section;
   a panel unit housing a radiation detection panel;
   a connection member that rotatably connects one edge portion of each of the control unit and the panel unit so as to adopt two states: a closed state in which one face of the control unit faces one face of the panel unit, and an open state in which the one face of the control unit and the one face of the panel unit are side-by-side facing in substantially the same direction, wherein in the open state the other face of the panel unit is positioned higher than the other face of the control unit; and
   a support member positioned below the other face of the panel unit and supporting the panel unit when in the open state.

2. The radiographic imaging apparatus of claim 1, wherein the support member is configured so as to be attachable to and detachable from the panel unit.

3. The radiographic imaging apparatus of claim 1, wherein in the open state, the one face of the control unit that faces the panel unit in the closed state and the one face of the panel unit are at substantially the same height.

4. The radiographic imaging apparatus of claim 1, wherein the support member is a member comprising a grid that removes scattered rays of radiation due to an imaging subject during image capture.

5. The radiographic imaging apparatus of claim 1, wherein the support member is a member comprising metal that prevents back scattering during image capture.

6. The radiographic imaging apparatus of claim 1, wherein the support member is a member comprising a battery.

7. The radiographic imaging apparatus of claim 1, wherein the support member is a handle provided at a peripheral edge portion of the panel unit.

8. The radiographic imaging apparatus of claim 1, wherein the radiation detection panel is capable of detecting radiation from both a front face and a back face.

9. The radiographic imaging apparatus of claim 8, further comprising a detection component for detecting whether the control unit and the panel unit are in the closed state or the open state, wherein the control section controls such that still image capture is performed in cases in which the closed state has been detected by the detection component, and controls such that video image capture is performed in cases in which the open state has been detected.

10. The radiographic imaging apparatus of claim 1, wherein the control unit comprises, on the one face, an operation section, a display section, or a combination thereof.

11. The radiographic imaging apparatus of claim 1, wherein the support member is displaceably configured so as to be inset to the control unit when in the closed state, and to be positioned below the other face of the panel unit when in the open state.

12. The radiographic imaging apparatus of claim 1, wherein the radiation detection panel comprises a substrate formed with switch elements and layered with a charge generation layer that generates charge by irradiation with radiation, the switch elements being configured to accumulate charge generated by the charge generation layer and read out the charge, with the radiation detection panel installed in the panel unit such that the charge generation layer is on the one face side of the panel unit.

13. The radiographic imaging apparatus of claim 1, wherein an amplification circuit for amplifying an electrical signal output from a radiation detection panel, an A/D converter for converting the electrical signal amplified by the amplification circuit to digital image data, or a combination thereof, is provided inside the connection member.

14. The radiographic imaging apparatus of claim 1, wherein the control unit further comprises a communication section that performs communication with an external device.

15. The radiographic imaging apparatus of claim 14, wherein the communication section is a wireless communication section that performs wireless communication with the external device.

16. The radiographic imaging apparatus of claim 1, wherein a surface of the control unit is formed in an undulating shape.

17. The radiographic imaging apparatus of claim 1, wherein a thickness of the panel unit is thinner than a thickness of the control unit.

18. The radiographic imaging apparatus of claim 1, wherein:
the radiation detection panel is configured such that radiation is converted into light in a scintillator for converting radiation into light and the radiation detection panel outputs an electrical signal expressing a radiographic image representation of this light; and
the scintillator is configured including columnar crystals of a fluorescent material.

19. The radiographic imaging apparatus of claim 18, wherein the fluorescent material is CsI.

* * * * *